United States Patent
Fujii et al.

(10) Patent No.: US 10,898,061 B2
(45) Date of Patent: Jan. 26, 2021

(54) ENDOSCOPE MAGNIFICATION OPTICAL SYSTEM, ENDOSCOPE, AND ENDOSCOPE SYSTEM

(71) Applicant: HOYA CORPORATION, Tokyo (JP)

(72) Inventors: Hiroaki Fujii, Tokyo (JP); Sachiko Nasu, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 169 days.

(21) Appl. No.: 16/077,909

(22) PCT Filed: Feb. 21, 2017

(86) PCT No.: PCT/JP2017/006296
§ 371 (c)(1),
(2) Date: Aug. 14, 2018

(87) PCT Pub. No.: WO2017/146021
PCT Pub. Date: Aug. 31, 2017

(65) Prior Publication Data
US 2019/0053695 A1  Feb. 21, 2019

(30) Foreign Application Priority Data

Feb. 23, 2016  (WO) .................. PCT/JP2016/055251

(51) Int. Cl.
*A61B 1/00* (2006.01)
*G02B 23/26* (2006.01)
(Continued)

(52) U.S. Cl.
CPC ............ *A61B 1/00188* (2013.01); *A61B 1/00* (2013.01); *A61B 1/00009* (2013.01);
(Continued)

(58) Field of Classification Search
CPC ... A61B 1/00188; A61B 1/00; A61B 1/00009; A61B 1/00096; A61B 1/04; A61B 1/06;
(Continued)

(56) References Cited

U.S. PATENT DOCUMENTS

| 5,357,374 A | 10/1994 | Ohno |
| 9,962,070 B2* | 5/2018 | Terakawa ........... A61B 1/00009 |

(Continued)

FOREIGN PATENT DOCUMENTS

| JP | S64-024214 | 1/1989 |
| JP | H05-323190 A | 12/1993 |

(Continued)

OTHER PUBLICATIONS

Office Action issued in Japanese family member Patent Appl. No. 2018-501691, dated Aug. 1, 2019.
(Continued)

*Primary Examiner* — Collin X Beatty
(74) *Attorney, Agent, or Firm* — Greenblum & Bernstein, P.L.C.

(57) ABSTRACT

An endoscope magnification optical system includes, in order from an object side, a first lens group having a negative power, a second lens group having a positive power, and a third lens group having a meniscus lens with a convex surface facing the object side. A distance from a lens surface of the first lens group that is nearest to the object side to an image surface is kept constant while the second lens group is moved in an optical axis direction with respect to the first lens group and the third lens group, which are fixed lens groups, and thereby an optical image is magnified.

11 Claims, 15 Drawing Sheets

(51) Int. Cl.
G02B 15/16 (2006.01)
A61B 1/04 (2006.01)
G02B 7/08 (2006.01)
G02B 13/18 (2006.01)
G02B 15/24 (2006.01)
A61B 1/06 (2006.01)

(52) U.S. Cl.
CPC ............ *A61B 1/00096* (2013.01); *A61B 1/04* (2013.01); *G02B 7/08* (2013.01); *G02B 13/18* (2013.01); *G02B 15/16* (2013.01); *G02B 15/24* (2013.01); *G02B 23/26* (2013.01); *A61B 1/06* (2013.01)

(58) Field of Classification Search
CPC .......... G02B 7/08; G02B 13/18; G02B 15/16; G02B 15/24; G02B 23/26
USPC ........................................ 359/689
See application file for complete search history.

(56) References Cited

U.S. PATENT DOCUMENTS

| | | | |
|---|---|---|---|
| 10,036,883 | B2 | 7/2018 | Fujii |
| 10,088,666 | B2 | 10/2018 | Nasu et al. |
| 2003/0189768 | A1 | 10/2003 | Murayama |
| 2005/0013016 | A1 | 1/2005 | Nakatani et al. |
| 2005/0231817 | A1 | 10/2005 | Matsusaka et al. |
| 2007/0070523 | A1 | 3/2007 | Noda |
| 2010/0020293 | A1 | 1/2010 | Yamamoto |
| 2011/0211267 | A1 | 9/2011 | Takato |
| 2014/0320978 | A1 | 10/2014 | Chou et al. |
| 2015/0042773 | A1* | 2/2015 | Uzawa ............... A61B 1/00096 348/65 |
| 2016/0282592 | A1* | 9/2016 | Abe .................... G02B 15/163 |
| 2017/0303774 | A1 | 10/2017 | Nasu |
| 2018/0003944 | A1 | 1/2018 | Fujii |

FOREIGN PATENT DOCUMENTS

| | | |
|---|---|---|
| JP | H10-048519 | 2/1998 |
| JP | 2005-037576 A | 2/2005 |
| JP | 2005-292403 A | 10/2005 |
| JP | 3845331 B2 | 11/2006 |
| JP | 2007-093961 A | 4/2007 |
| JP | 2010-032567 A | 2/2010 |
| JP | 4819969 B2 | 11/2011 |
| WO | 2010/119640 A1 | 10/2010 |
| WO | 2014/129089 A1 | 8/2014 |
| WO | 2017/043352 A1 | 3/2017 |

OTHER PUBLICATIONS

International Search Report issued in WIPO Patent Application No. PCT/JP2017/006296, dated May 16, 2017, along with an English translation thereof.

* cited by examiner (a)

(b)

(a)

(b)

(a) Spherical aberration / Chromatic aberration (A), Magnification chromatic aberration (B), Astigmatism (C), Distortion (D)

(b) Spherical aberration / Chromatic aberration (A), Magnification chromatic aberration (B), Astigmatism (C), Distortion (D)

(a)

| Spherical aberration Chromatic aberration | Magnification chromatic aberration | Astigmatism | Distortion |
| A | B | C | D |

(b)

| Spherical aberration Chromatic aberration | Magnification chromatic aberration | Astigmatism | Distortion |
| A | B | C | D |

ENDOSCOPE MAGNIFICATION OPTICAL SYSTEM, ENDOSCOPE, AND ENDOSCOPE SYSTEM

TECHNICAL FIELD

The present invention relates to an endoscope magnification optical system, an endoscope, and an endoscope system.

BACKGROUND ART

In the medical field, an endoscope (fiberscope or electronic endoscope) is commonly known and applied in practical use as a device for observing the body cavity interior of a patient. An endoscope in which a magnification optical system having a magnification function is mounted in order to precisely observe lesions is an example of this kind of endoscope.

For example, Japanese Patent No. 3845331 (hereinafter described as "Patent Document 1") describes a specific configuration of an endoscope magnification optical system. The endoscope magnification optical system according to Patent Document 1 is provided with, in order from the object side: a first lens group having a negative power, a second lens group having a positive power, a third three-lens group having a positive power, and a fourth lens group having a negative power, and the focal length of the entire system can be changed while the in-focus state is maintained, due to the second and third lens groups being moved while the object distance is changed, without changing the overall length from the first length group to the object surface.

SUMMARY OF INVENTION

In recent years, a solid-state image sensor mounted in an electronic device such as an electronic endoscope has become suitable for a short exit pupil distance in order to satisfy demand for a reduction in size. On the other hand, the endoscope magnification optical system according to Patent Document 1 has a long exit pupil distance due to the fact that a light beam emitted from the third lens group is incident at a position on the object-side surface (concave surface) of the fourth lens group (meniscus lens) with a comparatively low light beam height and is refracted with a strong positive power at a position on the image-side surface (convex surface) with a comparatively high light beam height. For this reason, when the endoscope magnification optical system according to Patent Document 1 and the solid-state image sensor with the configuration suitable for a short exit pupil distance are combined, a light beam with a small angle (a light beam that is close to being telecentric) is incident on peripheral pixels of the solid-state image sensor, and therefore a problem is indicated in which the light from the subject is not taken in efficiently in the peripheral pixels.

The present invention has been made in view of the foregoing circumstance and it is an object thereof to provide an endoscope magnification optical system suitable for a solid-state image sensor for a short exit pupil distance, an endoscope including the endoscope magnification optical system, and an endoscope system including the endoscope.

An endoscope magnification optical system according to an embodiment of the present invention includes, in order from an object, side: a first lens group having a negative power; a second lens group having a positive power; and a third lens group having a meniscus lens with a convex surface facing the object side, wherein a distance from a lens surface of the first lens group that is nearest to the object side to an image surface is kept constant while the second lens group is moved in an optical axis direction with respect to the first lens group and the third lens group, which are fixed lens groups, and thereby an optical image is magnified.

The endoscope magnification optical system according to an embodiment of the present invention may also have a configuration in which if the magnification of the second lens group at a telephoto end is defined as $m_{2t}$ and the magnification of the second lens group at a wide angle end is defined as $m_{2w}$, the following conditional equation is satisfied:

$$-1 < m_{2t} < m_{2w} < -0.35.$$

The endoscope magnification optical system according to an embodiment of the present invention may also have a configuration in which if the focal length of the third lens group is defined as $f_3$ (units: mm) and the composite focal length of first to third lens groups at the wide angle end is defined as $f_w$ (units: mm), the following equation is satisfied:

$$4 < f_3/f_w < 11.$$

The endoscope magnification optical system according to an embodiment of the present invention may also have a configuration in which the following conditional equation is satisfied:

$$6 < f_3/f_w < 10.$$

Also, in an embodiment of the present invention, the first lens group includes two lenses having negative powers and a lens having a positive power, for example.

The endoscope magnification optical system according to an embodiment of the present invention may also have a configuration in which if the focal length of the second lens group is defined as $f_2$ (units: mm) and the focal length of the third lens group is defined as $f_3$ (units: mm), the following equation is satisfied:

$$0.2 < f_2/f_3 < 0.7.$$

The endoscope magnification optical system according to an embodiment of the present invention may also have a configuration in which the following conditional equation is satisfied:

$$0.2 < f_2/f_3 < 0.4.$$

The endoscope magnification optical system according to an embodiment of the present invention may also have a configuration in which if the focal length of the first lens group is defined as $f_1$ (units: mm) and the focal length of the third lens group is defined as $f_3$ (units: mm), the following equation is satisfied:

$$0.7 < |f_3/f_1| < 3.5.$$

The endoscope magnification optical system according to an embodiment of the present invention may also have a configuration in which the following conditional equation is satisfied:

$$1.2 < |f_3/f_1| < 3.2.$$

The endoscope magnification optical system according to an embodiment of the present invention may also have a configuration including an aperture configured to move integrally with the second lens group on an optical axis between the first and the second lens groups.

An endoscope according to an embodiment of the present invention is a device with a leading end in which the above-described endoscope magnification optical system is incorporated.

Also, an endoscope system according to an embodiment of the present invention includes: the above-described endoscope; a light source apparatus configured to supply irradiated light to the above-described endoscope; and an image processing apparatus configured to process an image signal output by the above-described endoscope.

According to an embodiment of the present invention, an endoscope magnification optical system suitable for a solid-state image sensor for a short exit pupil distance, an endoscope including the endoscope magnification optical system, and an endoscope system including the endoscope are provided.

DESCRIPTION OF EMBODIMENTS

Hereinafter, an endoscope magnification optical system according to an embodiment of the present invention, an electronic endoscope in which the endoscope magnification optical system is incorporated, and an endoscope system including the electronic endoscope will be described with reference to the drawings.

Figure 1:
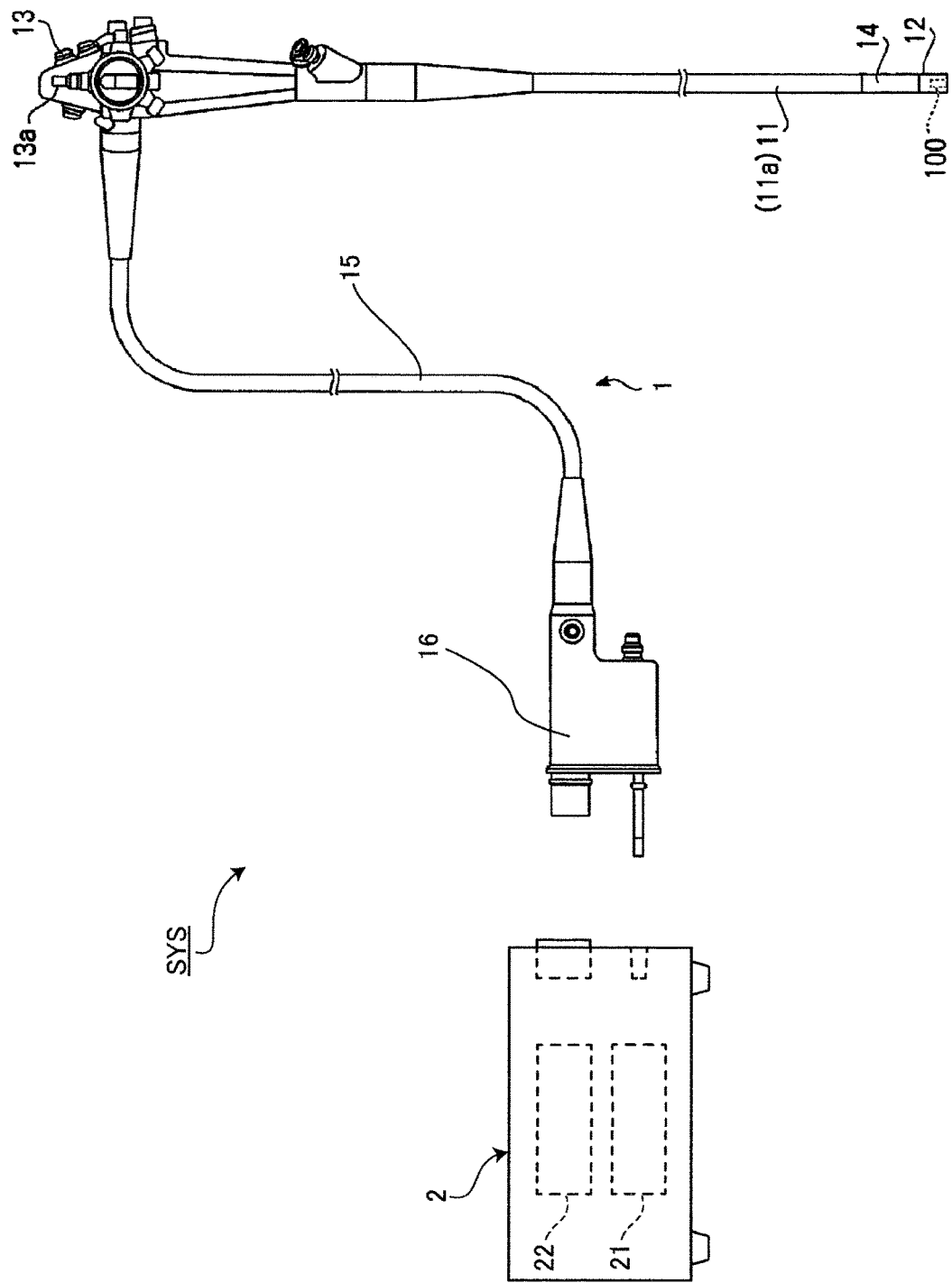
FIG. 1 is an external view showing an exterior of an electronic endoscope according to an embodiment of the present invention.

FIG. 1 is an external view showing an exterior of an endoscope system SYS according to an embodiment of the present invention. As shown in FIG. 1, the endoscope system SYS includes an electronic endoscope 1 and a processor 2.

The electronic endoscope 1 includes an insertion portion flexible tube 11 covered by a flexible sheath 11a. The leading end portion (curving portion 14) of the insertion portion flexible tube 11 curves in response to a remote operation (specifically, an operation of rotating a curving operation knob 13a) from a handheld operation portion 13 connected to the base end of the insertion portion flexible tube 11. The curving mechanism is a known mechanism incorporated in a common endoscope, and causes the curving portion 14 to curve by pulling an operation wire in conjunction with a rotation operation of the curving operation knob 13a. The base end of the leading end portion 12 covered by a rigid housing made of resin is coupled to the leading end of the curving portion 14. The region imaged by the electronic endoscope 1 moves due to the direction of the leading end portion 12 changing in response to a curving operation performed using the rotation operation of the curving operation knob 13a.

An endoscope magnification optical system 100 (a block indicated by broken lines in FIG. 1) is incorporated in the interior of the housing made of resin of the leading end portion 12. In order to acquire image data of a subject in the imaging region, the endoscope magnification optical system 100 allows the light from the subject to form an image on a light receiving surface of a solid-state image sensor (not shown). Examples of a solid-state image sensor include a CCD (Charge Coupled Device) image sensor and a CMOS (Complementary Metal Oxide Semiconductor) image sensor.

A universal cable 15 extends from the handheld operation portion 13 and a connector portion 16 is connected to the base end of the universal cable 15. The connector portion 16 is electrically and optically connected to a connector portion provided on a front panel surface of the processor 2.

The processor 2 is provided with a light source apparatus 21 and an image processing apparatus 22. A high-luminosity lamp such as a xenon lamp, a halogen lamp, a mercury lamp, or a metal halide lamp, or a semiconductor light emitting apparatus such as an LED (Light Emitting Diode) or LD (Laser Diode) is incorporated in the light source apparatus 21. Irradiated light irradiated from the light source apparatus 21 is transmitted through an LCB (Light Carrying Bundle) of the electronic endoscope 1 (i.e., the irradiated light is supplied to the electronic endoscope 1), is emitted from an emission end surface of the LCB arranged in the leading end portion 12, and is irradiated to biological tissue in the body cavity via a light distribution lens arranged on the leading end surface of the leading end portion 12. Optical feedback from the subject irradiated with the irradiated light forms an optical image on the light receiving surface of the solid-state image sensor via the endoscope magnification optical system 100.

The solid-state image sensor accumulates the optical images formed by the pixels on the light receiving surface as electric charges corresponding to amounts of light, and outputs the electric charges as an image signal. The image signal output by the solid-state image sensor is output to the image processing apparatus 22 via a driver circuit provided in the connector portion 16. The image processing apparatus 22 carries out predetermined signal processing such as demosaic processing, matrix calculation, and Y/C separation on the input image signal, and thereafter generates display image data and converts the generated display image data into a predetermined video format. The converted video format signal is output to a display device (not shown) such as a monitor. Accordingly, an image of the body cavity interior is displayed on a display screen of the display apparatus.

In the present embodiment, the light source apparatus 21 and the image processing apparatus 22 are provided in the processor 2, but in another embodiment, the light source apparatus 21 and the image processing apparatus 22 may be included as separate apparatuses.

Figure 2:
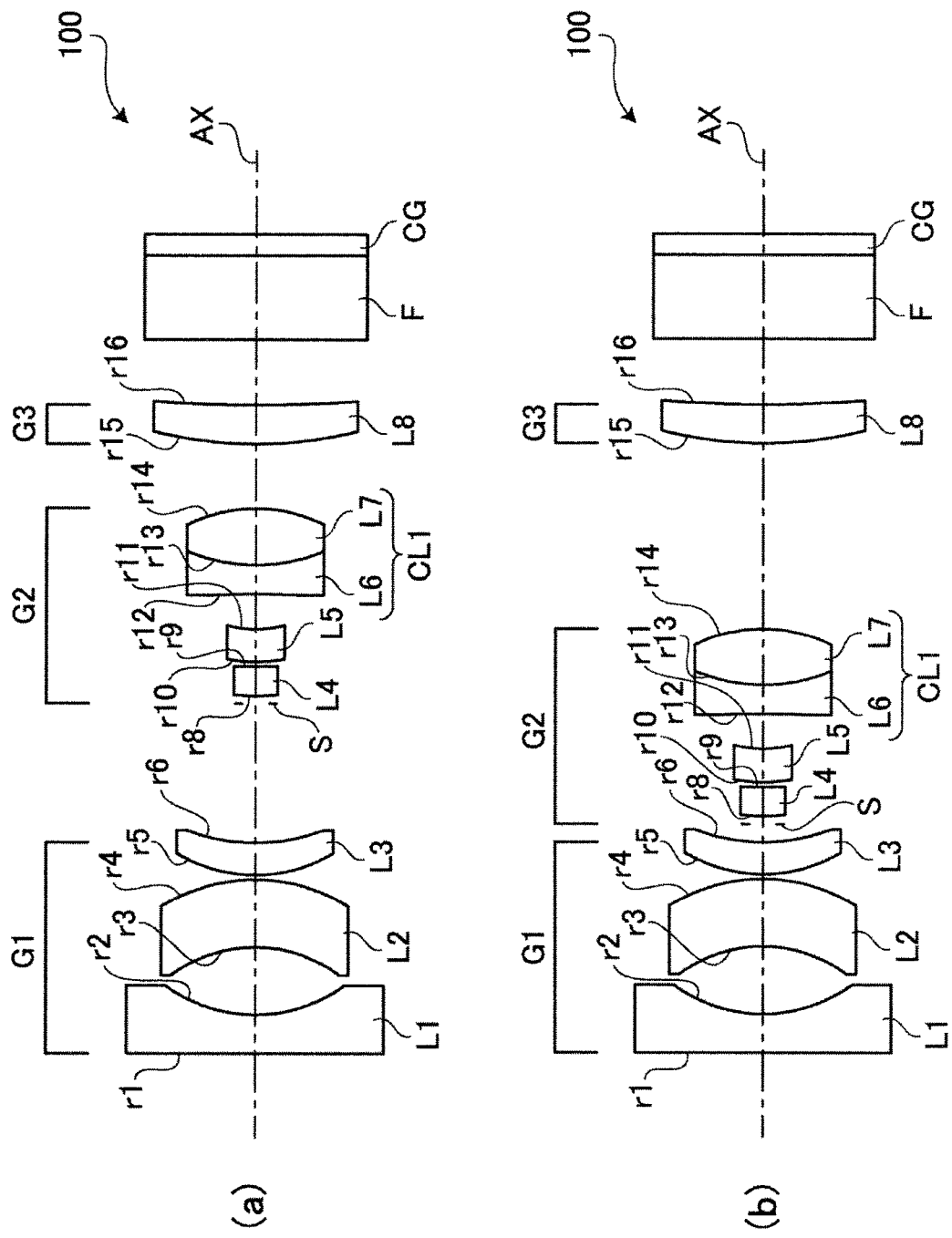
FIG. 2 is a lens arrangement diagram showing a configuration of an endoscope magnification optical system according to Example 1 of the present invention.

FIG. 2 is a cross-sectional view showing the endoscope magnification optical system 100 according to Example 1 (to be described in detail later) of the present invention and an arrangement of optical components arranged downstream thereof. FIGS. 2(a) and 2(b) are cross-sectional views showing respective lens arrangements for when the magnification position is at a wide angle end and a telephoto end. In the following description, the endoscope magnification optical system 100 according to an embodiment of the present invention will be described in detail with reference to FIG. 2.

As shown in FIG. 2, the endoscope magnification optical system 100 includes, in order starting from the object (subject) side, a first lens group G1 having a negative power, an aperture S, a second lens group G2 having a positive power, and a third lens group G3. The endoscope magnification optical system 100 is configured to change the focal length of the entire system (the composite focal length from the first lens group G1 to the third lens group) while holding the in-focus state and thus magnify the optical image by moving the second lens group G2 in an optical axis direction AX with respect to the first lens group G1 and the third lens group G3, which are fixed lens groups, while keeping the distance from the lens surface of the first lens group G1 that is nearest to the object to the image surface (i.e., the overall length of the endoscope magnification optical system 100) constant (always, regardless of object distance). The angle of view at the wide angle end of the endoscope magnification optical system 100 is 120 degrees or more (half angle of view is 60 degrees or more). The optical lenses constituting the lens groups G1 to G3 have shapes that are rotationally symmetrical about the optical axis AX of the endoscope magnification optical system 100. A color correction filter F for the solid-state image sensor is arranged downstream of the third lens group G3. The color correction filter F is adhered to a cover glass CG that protects the solid-state image sensor.

The handheld operation portion 13 is provided with a zoom button for operating a magnification mechanism. The operation signal sent when the zoom button has been operated is input to a drive control circuit mounted on a circuit board contained in the connector portion 16. The drive control circuit drives a motor arranged inside of the handheld operation portion 13 according to an operation signal. The driving of the motor is transmitted to a gear arranged in the leading end portion 12 via a gear connected to a motor and a torque wire that extends from the handheld operation portion 13 to the leading end portion 12. A cam moves in conjunction with the rotation of the gear arranged in the leading end portion 12, and a cam ring connected to the cam moves in the optical axis direction AX. The second lens group G2 is contained in the cam ring. That is, the second lens groups G2 moves in the optical axis direction AX in response to an operation of the zoom button by the user. Due to the second lens group G2 moving in the optical axis direction AX, the focal length of the entire system changes while the in-focus state is held, and thus the optical image is magnified.

That is, the electronic endoscope 1 includes a drive control circuit, a motor that is driven according to a control signal output by the drive control circuit, and a transmission mechanism (a gear connected to the motor, a torque wire, a gear in the leading end portion 12, a cam, and a cam ring) that transmits the driving force of the motor to the second lens group G2, and due to the driving force being transmitted to the second lens group G2, the second lens group G2 moves in the optical axis direction AX with respect to the first lens group G1 and the third lens group G3, which are fixed lens groups.

The first lens group G1 is a lens group that has a negative power and is arranged on the object side with respect to the aperture S. In the example shown in FIG. 2, the first lens group G1 includes two negative lenses and one positive lens. Specifically, the first lens group G1 includes at least, in order starting from the object side, a lens L1 having a negative power, a lens L2 having a negative power, and a lens L3 having a positive power. "Includes at least" is written because in the scope of the technical idea of the present invention, a configuration example is also possible in which other optical elements such as parallel flat plates are additionally arranged. The expression "includes at least" is used also in the descriptions for the second lens group G2 and the third lens group G3 for the same reason. Thus, due to the first lens group G1 having a configuration in which the negative power is dispersed in the group and the first lens group G1 has a positive power, the occurrence of a comatic aberration and a chromatic aberration is favorably suppressed. Accordingly, aberrational variation in the entire system is suppressed, and a favorable aberration performance is maintained from the wide angle end to the telephoto end.

Note that in the example of FIG. 2(a), the first lens group G1 includes three lenses overall, but in another example, the first lens group G1 can also include two lenses (e.g., later-described Examples 6 and 7). Also, the lenses L2 and L3 may be included as a cemented lens (e.g., later-described Example 5).

The second lens group G2 is a lens group that has a positive power and is arranged directly behind the aperture S. In the example shown in FIG. 2, the second lens group G2 includes at least, in order starting from the object side, lenses L4 and L5, and a cemented lens CL1. The cemented lens CL1 is obtained by bonding a positive and a negative lens (lenses L6 and L7) in order to suppress change in the chromatic aberration. In the example shown in FIG. 2, the negative lens (lens L5) is arranged on the object side, and the positive lens (lens L6) is arranged on the image side in the cemented lens CL1, but in another embodiment, the positive lens may be arranged on the object side and the negative lens may be arranged on the image side.

The second lens group G2 moves in the optical axis AX direction integrally with the aperture S in order to magnify the optical image formed on the light receiving surface of the solid-state image sensor. Due to the second lens group G2 and the aperture S being moved integrally, generation of astigmatism when at the telephoto end can be effectively suppressed. Note that in the example of FIG. 2(a), the second lens group G2 includes four lenses overall, but in another example, the second lens group G2 can also include three lenses (e.g., later-described Example 3). Also, the second lens group G2 may be constituted by two cemented lenses (e.g., later-described Example 4).

The aperture S is a plate-shaped member having a predetermined circular opening centered on the optical axis AX, or is a light-blocking film that coats the lens surface located the closest to the aperture S of the second lens group G2 (in the configuration example shown in FIG. 2, surface r8 on the object side of the positive lens L4), excluding a predetermined circular region centered on the optical axis AX. The thickness of the aperture S is very small compared to the thicknesses of the optical lenses included in the endoscope magnification optical system 100 and may be ignored when calculating the optical performance of the endoscope magnification optical system 100. For this reason, in the present specification, the thickness of the aperture S will be regarded as zero in the following description.

The third lens group G3 includes at least a meniscus lens (lens L8) that has a negative power and has a convex surface facing the object side. Illustratively, the third lens group G3 includes one lens (only a meniscus lens that has a positive power and has a convex surface facing the object side). If the third lens group G3 becomes eccentric with respect to the lenses, there is a risk that the aberration (in particular, astigmatism) will increase. If the third lens group G3 includes one lens, it is advantageous in that the occurrence of this kind of aberration can be avoided.

Also, the third lens group G3 may have a configuration in which a positive lens and a negative lens are arranged in the stated order starting from the object side. The positive lens has a power equal to that of the convex surface (object-side surface) of the meniscus lens with the single-lens configuration that has a positive power and has a convex surface facing the object side. The negative lens has a power equal to that of the convex surface (image-side surface) of the meniscus lens with the single-lens configuration that has a positive power and has a convex surface facing the object side. That is, the positive lens and the negative lens have a power equal to that of the lens L8.

Also, the third lens group G3 may be constituted by a meniscus lens that has a positive power and a convex surface facing the object side, and a lens having a negative power (a configuration of two lenses having a power equal to that of the lens L8).

In this manner, by arranging the meniscus lens (lens L8) that has a positive power and has a convex surface facing the object side on the image side of the second lens group G2, it is possible to suppress the influence on the focal length of the overall system, and to reduce image surface curvature (astigmatism). Also, by combining the thus-arranged lens L8 with the first lens group G1 having a design in which the negative power is strengthened in order to reduce the size, the Petzval sum approaches zero.

Also, in general, if a movable lens group having a positive power is moved to the telephoto end side, the meridional image plane is under the sagittal image plane, and thus astigmatism occurs. However, in the example shown in FIG. 2, due to the meniscus lens (lens L8) that has a positive power and has a concave surface facing the object side being arranged on the image side of the movable lens group (second lens group G2), when the second lens group G2 is moved to the telephoto end side, the peripheral light beam that passes through the lens 8 contributes to correcting the astigmatism.

For example, a configuration is considered in which a meniscus lens with a concave surface facing the object side is arranged as the final lens on the image side of the movable lens group. In this configuration, the light beam emitted from the movable lens is incident at a position at which the light beam height on the concave surface (object-side surface of the meniscus lens) is relatively low, and is refracted with a strong positive power at a position at which the light beam height on the convex surface (image-side surface of the meniscus lens) is relatively high. For this reason, the meridional image surface goes under, the exit pupil distance increases, and a light beam with a small angle (light beam that is close to being telecentric) is incident on the peripheral pixels of the solid-state image sensor. If the solid-state image sensor is for a short exit pupil distance, the light from the subject is not efficiently taken in at the peripheral pixels.

In contrast to this, in the example shown in FIG. 2, due to the final lens surface (image-side surface of the lens L8) of the endoscope magnification optical system 100 being a concave surface, the incidence angle of the light beam to the peripheral pixels of the solid-state image sensor can be made larger compared to the case where the final lens surface is a concave surface. For this reason, if the solid-state image sensor is for a short exit pupil distance, the light from the subject is efficiently taken in at the peripheral pixels. Also, since the exit pupil distance between the endoscope magnification optical system 100 and the solid-state image sensor is suitably reduced, the overall length of the leading end portion 12 of the electronic endoscope 1 can be made shorter.

Also, in the example shown in FIG. 2, the meniscus lens (lens L8) with the convex surface facing the object side is arranged as the third lens group G3, and thus the light beam emitted from the second lens group G2 is incident at a position at which the light beam height of the convex surface of the lens L8 is relatively high. For this reason, the light beam does not need to be significantly refracted in the first lens group G1 and the second lens group G2, and thus the powers of the first lens group G1 and the second lens group G2 are suppressed. In other words, the error sensitivity of the first lens group G1 and the second lens group G2 decreases, which contributes to improving yield.

In the case where the magnification of the second lens group G2 at the telephoto end is defined as $m_{2t}$ and the magnification of the second lens group G2 at the wide angle end is defined as $m_{2w}$, the endoscope magnification optical system 100 satisfies the following conditional equation (1):

$$-1 < m_{2t} < m_{2w} < -0.35 \tag{1}$$

Due to the conditional equation (1) being satisfied, the endoscope magnification optical system 100 can be given a configuration that is suitable for precise focus adjustment and can be given a compact design.

If the magnification $m_{2w}$ is greater than or equal to the value on the right side in conditional equation (1), the magnification $m_{2w}$ of the second lens group G2 at the wide angle side is low, and therefore the movement amount of the second lens group G2 that is needed for magnification increases, and the overall length of the endoscope magnification optical system 100 increases. As a result, since it is necessary to contain the endoscope magnification optical system 100 with a long overall length, the overall length of the leading end portion 12 of the electronic endoscope 1, which is a hard portion, needs to be made longer. Also, if the magnification $m_{2w}$ is greater than or equal to the value on the right, side in the conditional equation (1), the magnification $m_{2t}$ of the second lens group G2 at the telephoto end relatively increases, and therefore the change in the optimal object distance for when the second lens group G2 has been moved increases. For this reason, precise focus adjustment can no longer be performed.

Considering the user-friendliness of the electronic endoscope 1 when observing the body cavity interior, the optimal object distance preferably decreases as the telephoto end is approached from the wide angle end, and is preferably the shortest when at the telephoto end. However, if the magnification $m_{2t}$ is less than or equal to the value on the left side in the conditional equation (1), the optimal object distance reaches its minimum before the telephoto end is reached. For this reason, the user-friendliness of the electronic endoscope 1 at a time of observing the body cavity interior deteriorates.

If the focal length of the third lens group G3 is defined as $f_3$ (units: mm) and the focal length of the entire system at the wide angle end is defined as $f_w$ (units: mm), the endoscope magnification optical system 100 satisfies the following conditional equation (2):

$$4 < f_3/f_w < 11 \qquad (2)$$

Due to the conditional equation (2) being satisfied, various aberrations (mainly astigmatism, chromatic aberration, comatic aberration, and image surface curvature) are favorably corrected, and the occurrence of shading is suppressed.

If the value in the middle of the conditional equation (2) is greater than or equal to the value on the right side, the power of the third lens group G3 is too weak, and therefore it is difficult to favorably correct astigmatism. Also, if the value in the middle of the conditional equation (2) is greater than or equal to the value on the right side, chromatic aberration and comatic aberration increase due to the third lens group G3 having an excessively large meniscus shape.

If the value in the middle of the conditional equation (2) is less than or equal to the value on the left side, the power of the third lens group G3 is too strong, and the curvature of the concave surface is too small with respect to the curvature of the convex surface of the third lens group G3, and thus the Petzval sum increases and image surface curvature significantly occurs. Also, if the value in the middle of the conditional equation (2) is less than or equal to the value on the left side, the incidence angle of the light between the solid-state image sensors is too small, and thus shading occurs and the captured image deteriorates.

The endoscope magnification optical system 100 may further satisfy the following conditional equation (3):

$$6 < f_3/f_w < 10 \qquad (3)$$

Accordingly, various aberrations (mainly astigmatism, chromatic aberration, comatic aberration, and image surface curvature) are even more favorably corrected, and the occurrence of shading is even more suppressed.

In the case where the focal length of the second lens group G2 is defined as $f_2$ (units: mm), the endoscope magnification optical system 100 satisfies the following conditional equation (4):

$$0.2 < f_2/f_3 < 0.7 \qquad (4)$$

Due to the conditional equation (4) being satisfied, the endoscope magnification optical system 100 can be given a configuration that is suitable for precise focus adjustment and can be given a compact design.

In the case where the value in the middle of the conditional equation (4) is greater than or equal to the value on the right side, the negative power of the second lens group G2 is relatively too weak, and therefore the movement amount of the second lens group G2 increases, which is disadvantageous for reducing the size of the endoscope magnification optical system 100. Also, if the value in the middle of the conditional equation (4) is greater than or equal to the value on the right side, the effect of compressing the optical image formed by the third lens group G3 will be too strong. In order to relatively reduce the effect of compressing the optical image formed by the third lens group G3, the diameters of the first lens group G1 and the second lens group G2 need to be increased.

If the value in the middle of the conditional equation (4) is less than or equal to the value on the left side, the negative power of the second lens group G2 will be relatively strong, and the movement amount of the second lens group G2 will be smaller. For this reason, a focus adjustment needs to be performed by slightly moving the second lens group G2. For this reason, a high-precision focus adjustment mechanism is needed, which increases the cost and the size of the electronic endoscope 1. Also, if the value in the middle of the conditional equation (4) is less than or equal to the value on the left side, change in the incidence angle of the light on the solid-state image sensor when the magnification position is at the wide angle end or the telephoto end is more significant. For this reason, it is difficult to adapt to the shading characteristics of the solid-state image sensor.

The endoscope magnification optical system 100 may further satisfy the following conditional equation (5):

$$0.2 < f_2/f_3 < 0.4 \qquad (5)$$

Accordingly the endoscope magnification optical system 100 can have an even more suitable configuration for precise focus adjustment, and can be designed to be even more compact.

In the case where the focal length of the first lens group G1 is defined as $f_1$ (units: mm), the endoscope magnification optical system 100 satisfies the following conditional equation (6):

$$0.7 < |f_3/f_1| < 3.5 \qquad (6)$$

Due to the conditional equation (6) being satisfied, various aberrations (mainly astigmatism and image surface curvature) are favorably corrected, and the design can be made more compact.

In the case where the value in the middle of the conditional equation (6) is less than or equal to the value on the right side, the power of the first lens group G1 will be too strong, and therefore the Petzval sum will increase negatively and the astigmatism and image surface curvature will occur so significantly that they cannot be corrected by the third lens group G3.

In the case where the value in the middle of the conditional equation (6) is greater than or equal to the value on the left side, the power of the first lens group G1 is too weak, and therefore the diameter of the first lens group G1 needs to be made larger. Also, if the value in the middle of the conditional equation (6) is less than or equal to the value on the left side, the power of the third lens group G3 is too strong, and therefore the occurrence of comatic aberration will increase, and change in the incidence angle of the light on the solid-state image sensor when the magnification position is at the wide angle end or the telephoto end will be more significant. For this reason, it is difficult to adapt to the shooting characteristics of the solid-state image sensor.

The endoscope magnification optical system 100 may further satisfy the following conditional equation (7):

$$1.2 < |f_3/f_1| < 3.2 \qquad (7)$$

Accordingly, it is possible to use a configuration in which various aberrations (mainly astigmatism and image surface curvature) are even more suitably corrected, and an even smaller design is possible.

The endoscope magnification optical system 100 is suitable for a solid-state image sensor of 0.3 megapixels or more, for example. The endoscope magnification optical system 101 is more suitable for a solid-state image sensor of 1.0 megapixel or more, for example. The endoscope magnification optical system 100 is even more suitable for a solid-state image sensor of 1.0 to 2.0 megapixels, for example.

Next, seven examples using specific numeric values of the above-described endoscope magnification optical system 100 will be described. The endoscope magnification optical system 100 according to Examples 1 to 7 with specific numeric values is arranged in the leading end portion 12 of the electronic endoscope 1 shown in FIG. 1.

Example 1

As described above, the endoscope magnification optical system 100 according to Example 1 of the present invention is as shown in FIG. 2.

A configuration using specific numeric values (design values) of the endoscope magnification optical system 100 (and the optical components arranged downstream thereof) according to the present Example 1 is shown in Table 1. Surface numbers NO shown in the upper field (surface data) of Table 1 correspond to the surface numerals rn (n being an integer) shown in FIG. 2, except for surface number 7, which corresponds to the aperture S. In the upper field of Table 1, R (units: mm) indicates a radius of curvature of each surface of the optical members, D (units: mm) indicates the optical member thickness or optical member interval on the optical axis AX, N(d) indicates the refractivity of a d line (wavelength 588 nm), and vd indicates the Abbe number of the d line.

The lower field (various data) of Table 1 indicates the specifications (actual F number, focal length (units: mm) of the entire system, optical magnification, half angle of view (units: degrees), image height (units: mm), group interval D6 (units: mm), and group interval D14 (units: mm)) of the endoscope magnification optical system 100 according to the present Example 1, for the wide angle end and the telephoto end. The group interval D6 is the group interval between the first lens group G1 and the second lens group G2. The group interval D14 is the group interval between the second lens group G2 and the third lens group G3. The group interval D6 and the group interval D14 change according to the magnification position.

TABLE 1

| Example 1 | | | | |
|---|---|---|---|---|
| Image Data | | | | |
| NO | R | D | N(d) | vd |
| 1 | INFINITY | 0.460 | 1.88300 | 40.8 |
| 2 | 1.812 | 0.801 | | |
| 3 | −1.681 | 0.805 | 1.80611 | 40.7 |
| 4 | −2.106 | 0.058 | | |
| 5 | 1.850 | 0.378 | 1.74950 | 35.3 |
| 6 | 2.299 | D6 | | |
| 7 aperture | INFINITY | 0.092 | | |
| 8 | 2.231 | 0.345 | 1.80400 | 46.6 |
| 9 | 6.668 | 0.058 | | |
| 10 | 1.840 | 0.396 | 1.88300 | 40.8 |
| 11 | 1.365 | 0.416 | | |
| 12 | −10.619 | 0.345 | 1.84666 | 23.8 |
| 13 | 2.083 | 0.671 | 1.72916 | 54.7 |
| 14 | −1.834 | D14 | | |
| 15 | 5.034 | 0.460 | 1.72916 | 54.7 |
| 16 | 16.258 | 0.779 | | |

TABLE 1-continued

| Example 1 | | | | |
|---|---|---|---|---|
| 17 | INFINITY | 1.000 | 1.51407 | 73.4 |
| 18 | INFINITY | 0.250 | 1.51000 | 63.0 |
| 19 | INFINITY | — | | |

| Various data | | |
|---|---|---|
| | Wide angle | Telephoto |
| F number | 9.0 | 11.2 |
| Focal length | 1.29 | 1.77 |
| Magnification | −0.090 | −0.542 |
| Half angle of view | 70.7 | 40.6 |
| Image height | 1.32 | 1.32 |
| D6 | 1.658 | 0.218 |
| D14 | 0.765 | 2.205 |

Figure 3:
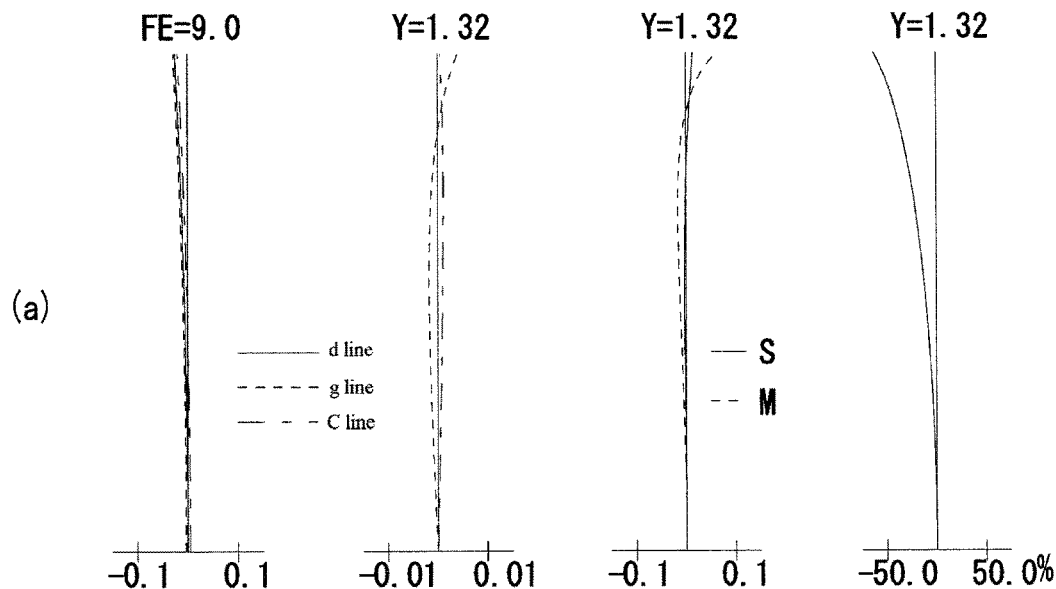
FIG. 3 is a diagram showing various aberrations in the endoscope magnification optical system according to Example 1 of the present invention.
Figure 3:
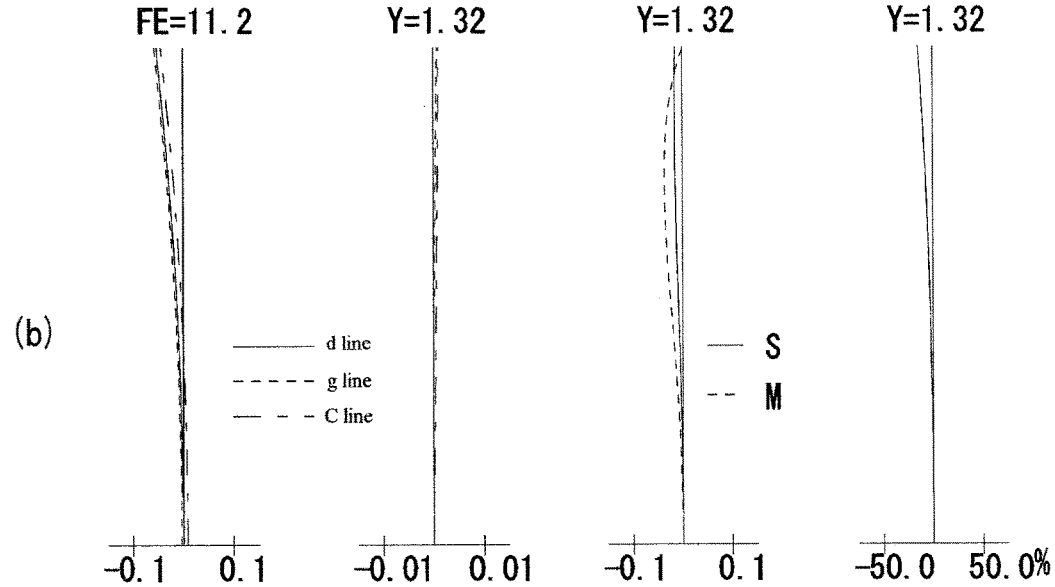

Graphs A to D in FIG. 3(a) are diagrams showing various aberrations when the magnification position is at the wide angle end in the endoscope magnification optical system 100 according to the present Example 1. Graphs A to D in FIG. 3(b) are diagrams showing various aberrations when the magnification position is at the telephoto end in the endoscope magnification optical system 100 according to the present Example 1. Graph A in FIGS. 3(a) and 3(b) shows a spherical aberration and an axial chromatic aberration at a d line, a g line (wavelength 436 nm), and a C line (wavelength 656 nm). Graph B in FIGS. 3(a) and 3(b) indicates a magnification chromatic aberration at the d line, g line, and C line. In graphs A and B, the solid lines indicate aberrations at the d line, the dotted lines indicate aberrations at the g line, and the single-dot chain line indicates aberrations at the C line. Graph C in FIGS. 3(a) and 3(b) indicates astigmatism. In graph C, the solid line indicates a sagittal component and the dotted line indicates a meridional component. Graph D in FIGS. 3(a) and 3(b) indicates distortion. The vertical axes in graphs A to C indicate the image height and the horizontal axes indicate the aberration amount. The vertical axis in graph D indicates the image height and the horizontal axis indicates the distortion rate. Note that the description of the tables and drawings of the present Example 1 is applied also to the tables and drawings presented in the following examples using numeric values.

The aberrations are favorably corrected at both the wide angle end and the telephoto end (see FIG. 3) and a meniscus lens with a convex surface facing the object side is arranged as the third lens group G3 (see FIG. 2 and Table 1), and thus the endoscope magnification optical system 100 according to Example 1 has a configuration that is suitable for a solid-state image sensor for a short exit pupil distance. Note that in the intermediate region between the wide angle end and the telephoto end, the various aberrations change within the ranges shown in FIGS. 3(a) and 3(b). That is, the endoscope magnification optical system 100 according to the present Example 1 has a favorable optical performance at any magnification position from the wide angle end to the telephoto end.

Example 2

Figure 4:
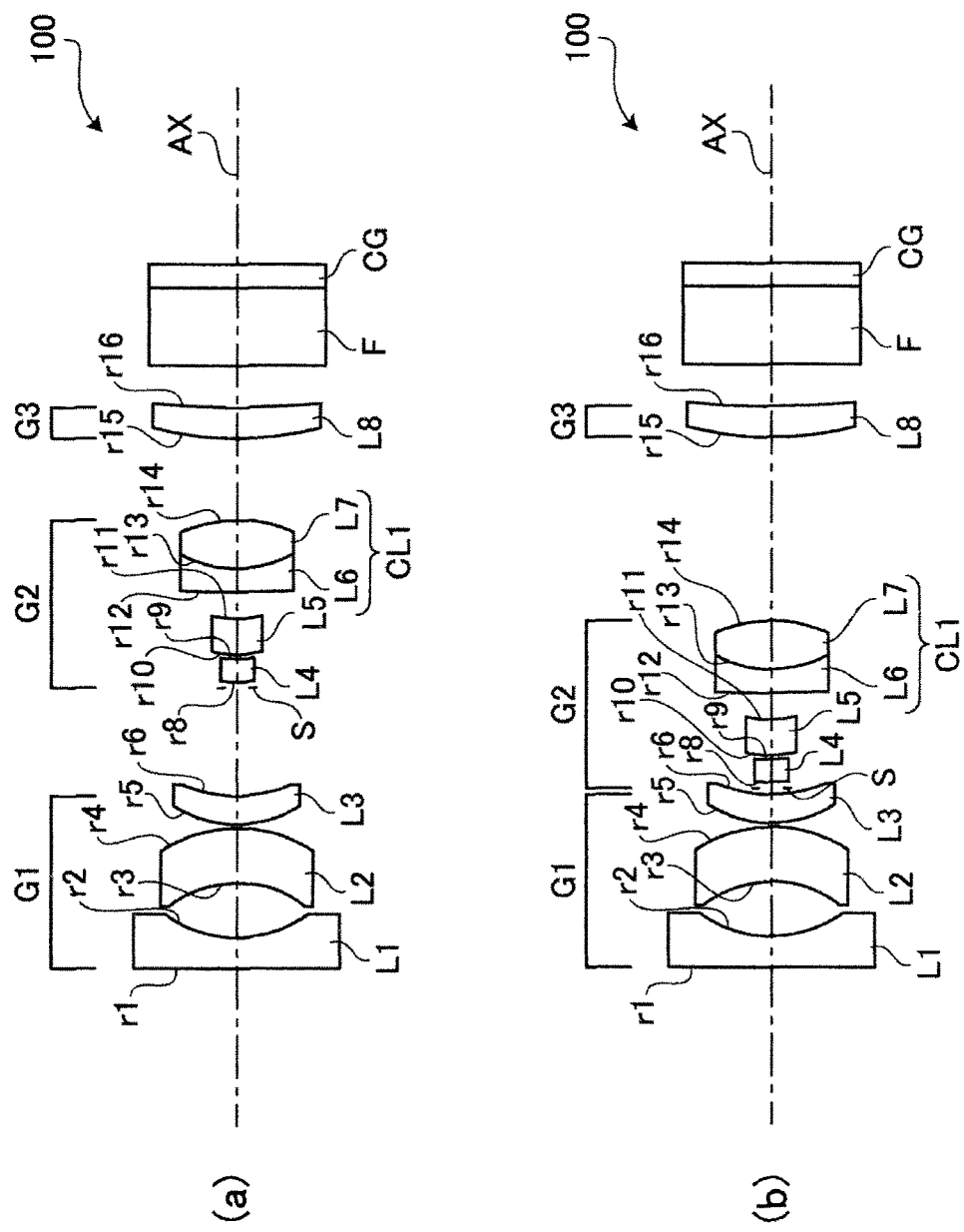
FIG. 4 is a lens arrangement diagram showing a configuration of an endoscope magnification optical system according to Example 2 of the present invention.

FIGS. 4(a) and 4(b) are cross-sectional views showing an arrangement of optical components including the endoscope magnification optical system 100 according to the present Example 2. FIG. 4(a) shows a lens arrangement when the magnification position is at the wide angle end. FIG. 4(b) shows a lens arrangement when the magnification position is at the telephoto end.

Figure 5:
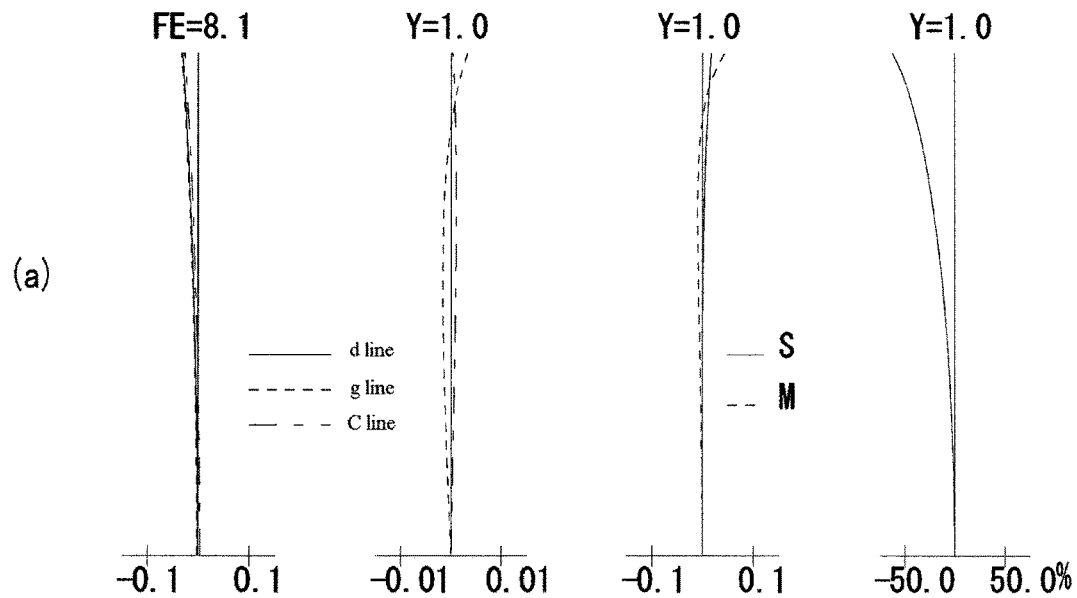
FIG. 5 is a diagram showing various aberrations in the endoscope magnification optical system according to Example 2 of the present invention.
Figure 5:
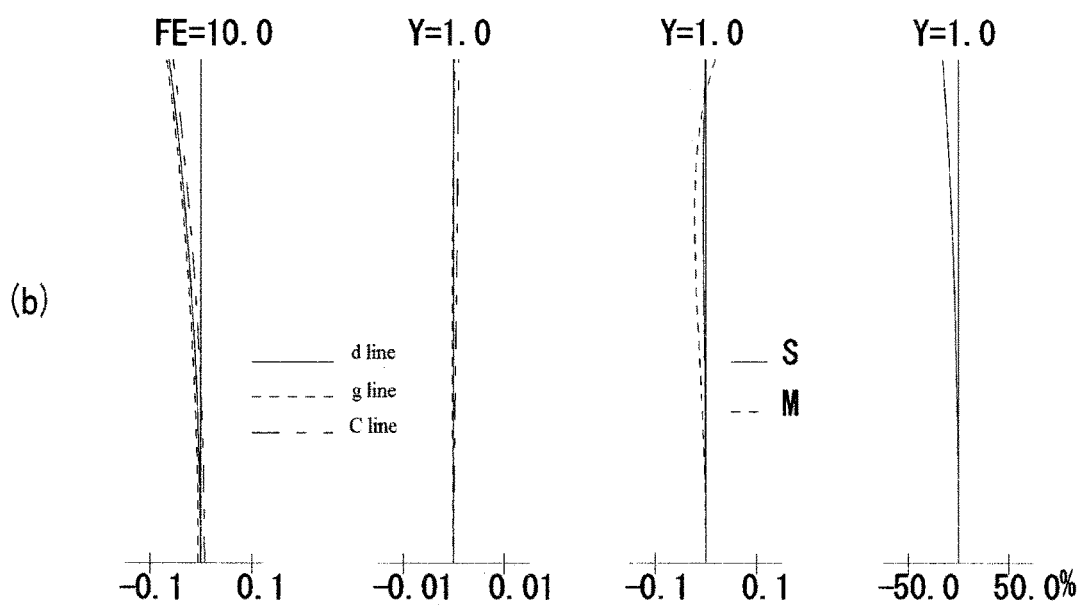

Graphs A to D in FIG. 5(a) are diagrams showing various aberrations when the magnification position is at the wide angle end in the endoscope magnification optical system 100 according to the present Example 2. Graphs A to D in FIG. 5(b) are diagrams showing various aberrations when the magnification position is at the telephoto end in the endoscope magnification optical system 100 according to the present Example 2.

Table 2 shows configurations and specifications using specific numeric values of optical components including the endoscope magnification optical system 100 according to the present Example 2. As can be understood from FIGS. 4 and 5 and Table 2, the endoscope magnification optical system 100 according to the present Example 2 has a favorable optical performance at any magnification position from the wide angle end to the telephoto end, and has a configuration that is suitable for a solid-state image sensor for a short exit pupil distance.

TABLE 2

Example 2

Image Data

| NO | R | D | N(d) | vd |
|---|---|---|---|---|
| 1 | INFINITY | 0.350 | 1.88300 | 40.8 |
| 2 | 1.372 | 0.619 | | |
| 3 | −1.251 | 0.613 | 1.80611 | 40.7 |
| 4 | −1.565 | 0.044 | | |
| 5 | 1.328 | 0.321 | 1.74950 | 35.3 |
| 6 | 1.571 | D6 | | |
| 7 aperture | INFINITY | 0.070 | | |
| 8 | 2.643 | 0.263 | 1.95906 | 17.5 |
| 9 | 2.469 | 0.044 | | |
| 10 | 1.220 | 0.404 | 1.88300 | 40.8 |
| 11 | 1.202 | 0.302 | | |
| 12 | 24.692 | 0.263 | 1.84666 | 23.8 |
| 13 | 1.338 | 0.547 | 1.77250 | 49.6 |
| 14 | −1.535 | D14 | | |
| 15 | 3.810 | 0.350 | 1.72916 | 54.7 |
| 16 | 9.976 | 0.470 | | |
| 17 | INFINITY | 0.876 | 1.51407 | 73.4 |
| 18 | INFINITY | 0.263 | 1.51000 | 63.0 |
| 19 | INFINITY | — | | |

Various data

| | Wide angle | Telephoto |
|---|---|---|
| F number | 8.1 | 10.0 |
| Focal length | 1.00 | 1.39 |
| Magnification | −0.091 | −0.553 |
| Half angle of view | 70.1 | 40.0 |
| Image height | 1.00 | 1.00 |
| D6 | 1.221 | 0.070 |
| D14 | 0.929 | 2.080 |

Example 3

Figure 6:
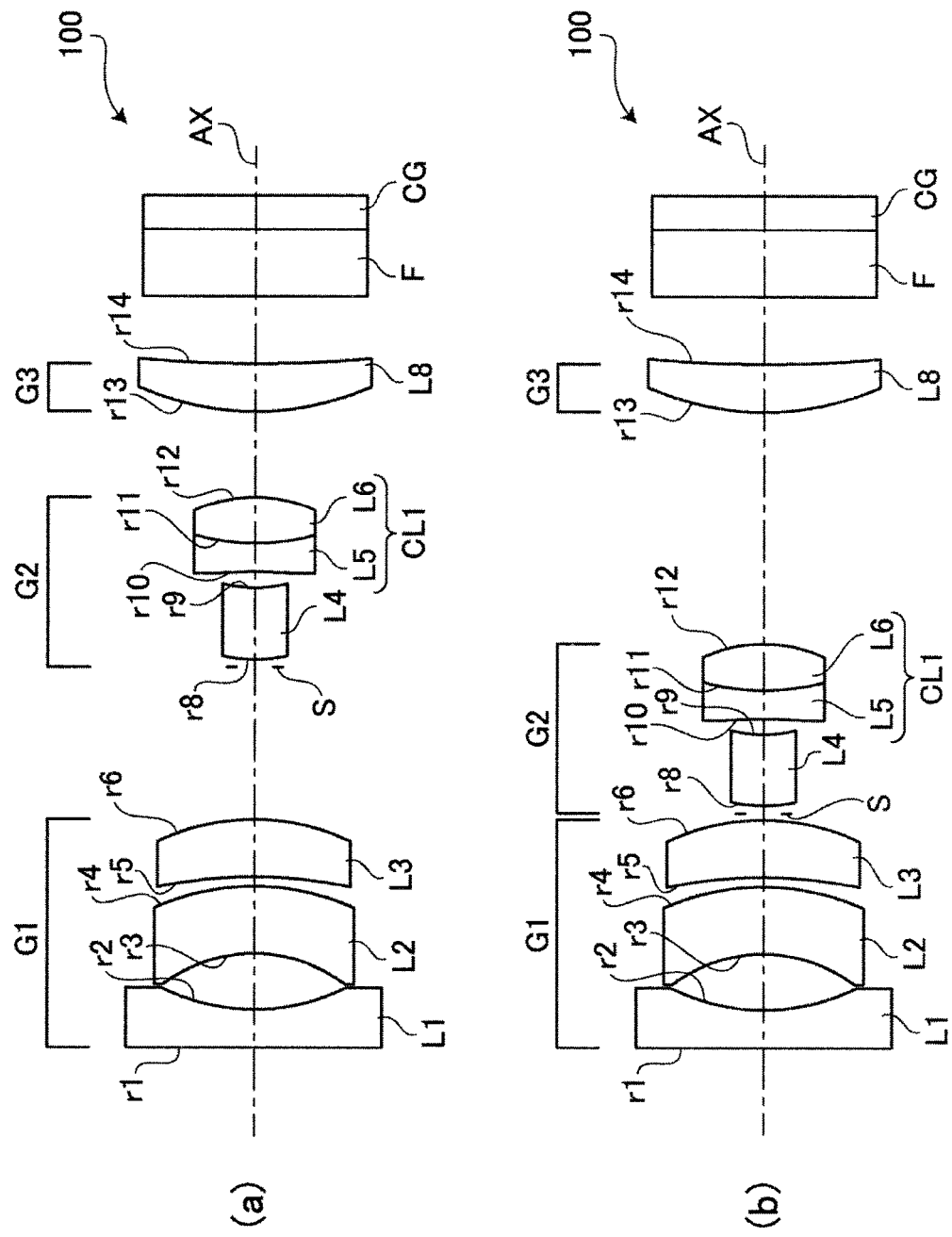
FIG. 6 is a lens arrangement diagram showing a configuration of an endoscope magnification optical system according to Example 3 of the present invention.

FIGS. 6(a) and 6(b) are cross-sectional views showing an arrangement of optical components including the endoscope magnification optical system 100 according to the present Example 3. FIG. 6(a) shows a lens arrangement when the magnification position is at the wide angle end. FIG. 6(b) shows a lens arrangement when the magnification position is at the telephoto end.

Figure 7:
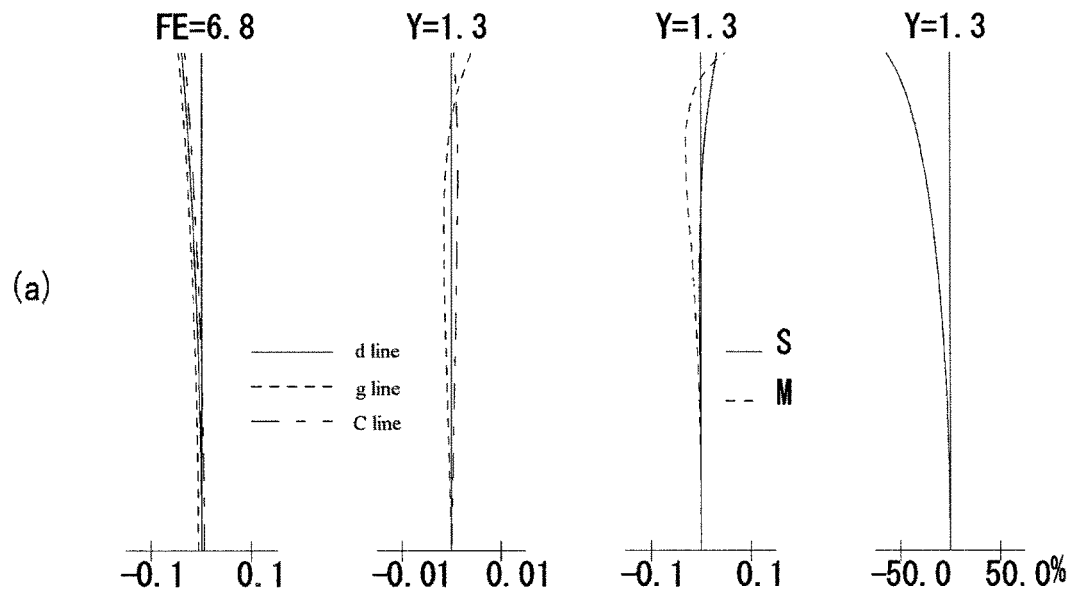
FIG. 7 is a diagram showing various aberrations in the endoscope magnification optical system according to Example 3 of the present invention.
Figure 7:
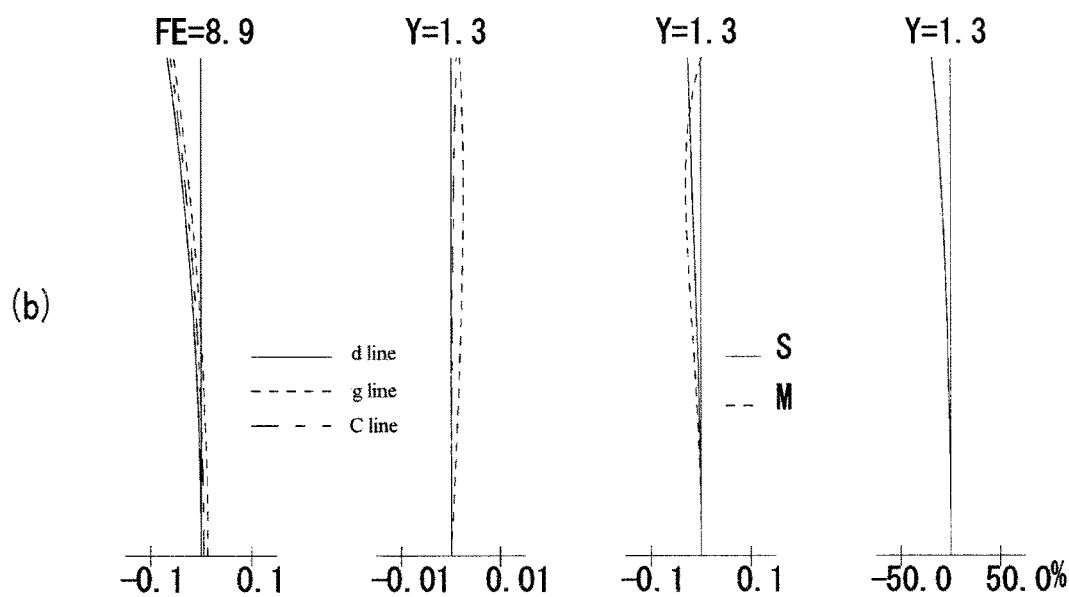

Graphs A to D in FIG. 7(a) are diagrams showing various aberrations when the magnification position is at the wide angle end in the endoscope magnification optical system 100 according to the present Example 3. Graphs A to D in FIG. 7(b) are diagrams showing various aberrations when the magnification position is at the telephoto end in the endoscope magnification optical system 100 according to the present Example 3.

Table 3 shows configurations and specifications using specific numeric values of optical components including the endoscope magnification optical system 100 according to the present Example 3. Note that in Table 3, the group interval between the second lens group G2 and the third lens group G3 is denoted by the reference numeral "D12". As can be understood from FIGS. 6 and 7 and Table 3, the endoscope magnification optical system 100 according to the present Example 3 has a favorable optical performance at any magnification position from the wide angle end to the telephoto end, and has a configuration that is suitable for a solid-state image sensor for a short exit pupil distance.

TABLE 3

Example 3

Image Data

| NO | R | D | N(d) | vd |
|---|---|---|---|---|
| 1 | INFINITY | 0.452 | 1.88300 | 40.8 |
| 2 | 2.426 | 0.663 | | |
| 3 | −1.781 | 0.791 | 1.84666 | 23.8 |
| 4 | −2.907 | 0.113 | | |
| 5 | −5.413 | 0.678 | 1.77250 | 49.6 |
| 6 | −2.647 | D6 | | |
| 7 aperture | INFINITY | 0.091 | | |
| 8 | 1.734 | 0.849 | 1.95906 | 17.5 |
| 9 | 1.599 | 0.186 | | |
| 10 | −5.791 | 0.339 | 1.92286 | 18.9 |
| 11 | 2.680 | 0.551 | 1.77250 | 49.6 |
| 12 | −1.717 | D12 | | |
| 13 | 3.390 | 0.565 | 1.72916 | 54.7 |
| 14 | 15.844 | 0.795 | | |
| 15 | INFINITY | 0.800 | 1.51407 | 73.4 |
| 16 | INFINITY | 0.400 | 1.51000 | 63.0 |
| 17 | INFINITY | — | | |

Various data

| | Wide angle | Telephoto |
|---|---|---|
| F number | 6.8 | 8.9 |
| Focal length | 1.31 | 1.85 |
| Magnification | −0.116 | −0.567 |
| Half angle of view | 71.2 | 41.5 |
| Image height | 1.30 | 1.30 |
| D6 | 1.813 | 0.080 |
| D12 | 1.017 | 2.750 |

Example 4

Figure 8:
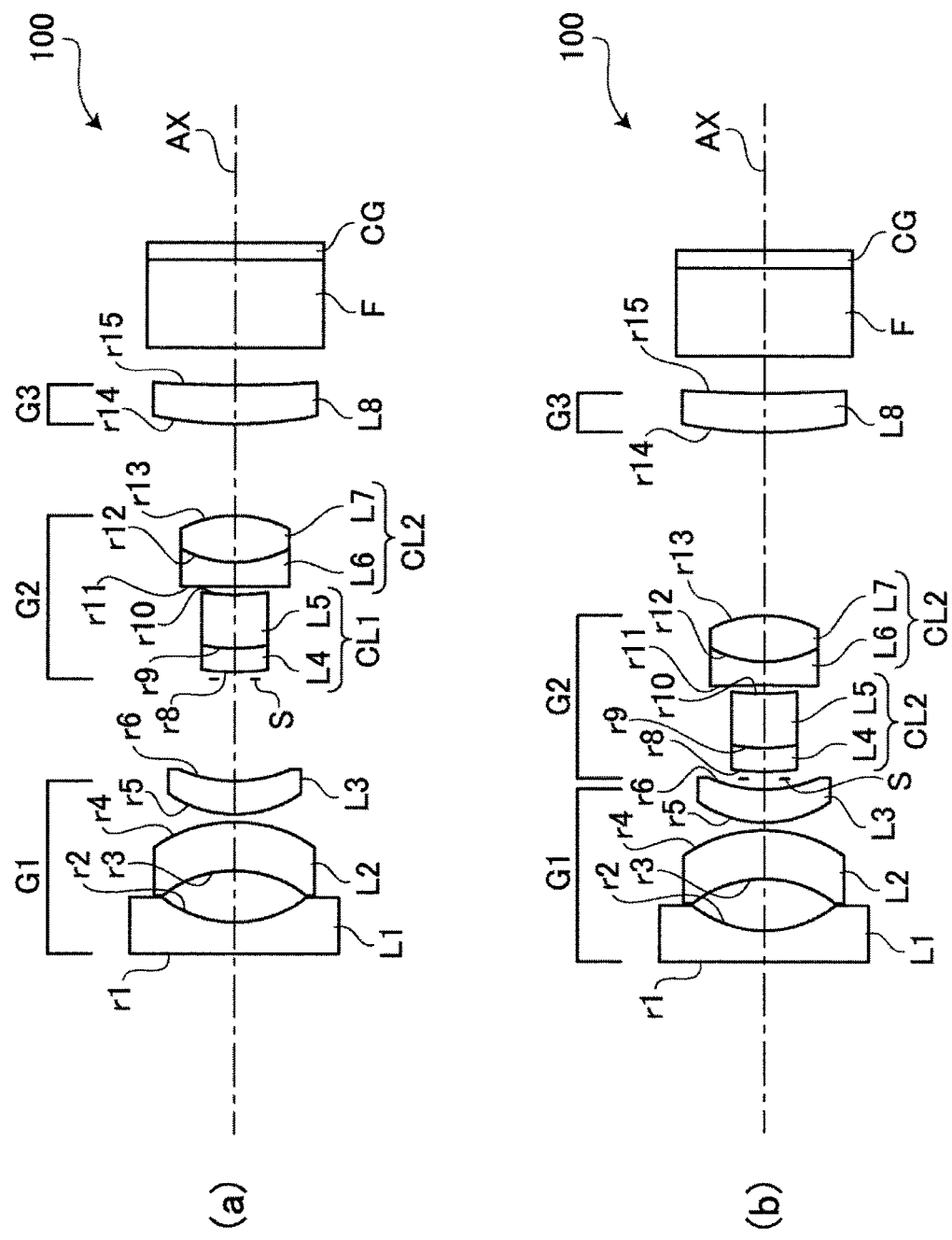
FIG. 8 is a lens arrangement diagram showing a configuration of an endoscope magnification optical system according to Example 4 of the present invention.

FIGS. 8(a) and 8(b) are cross-sectional views showing an arrangement of optical components including the endoscope magnification optical system 100 according to the present Example 4. FIG. 8(a) shows a lens arrangement when the magnification position is at the wide angle end. FIG. 8(b) shows a lens arrangement when the magnification position is at the telephoto end.

Figure 9:
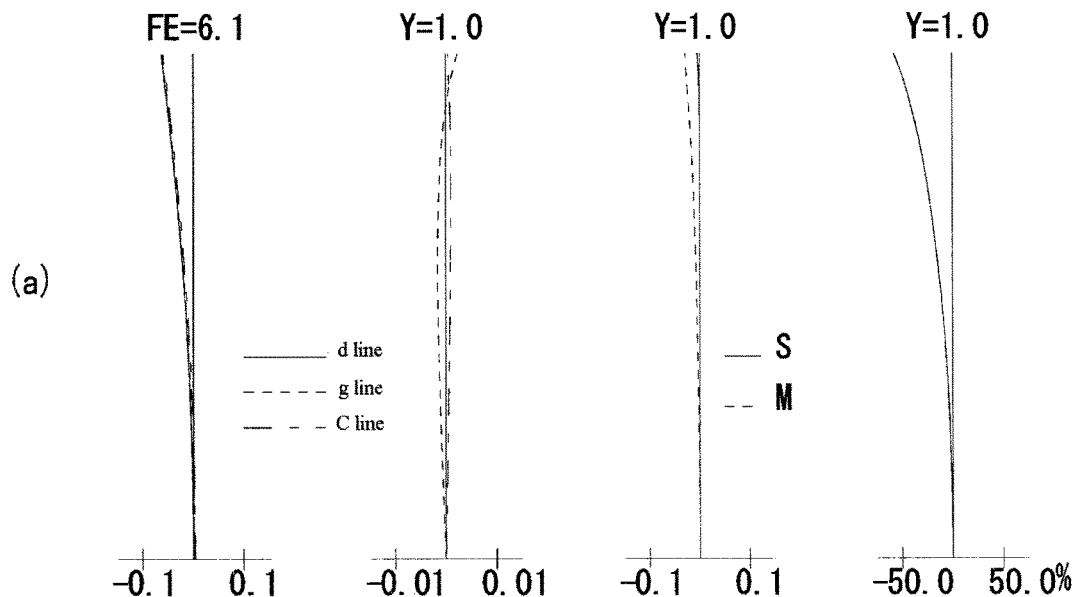
FIG. 9 is a diagram showing various aberrations in the endoscope magnification optical system according to Example 4 of the present invention.
Figure 9:
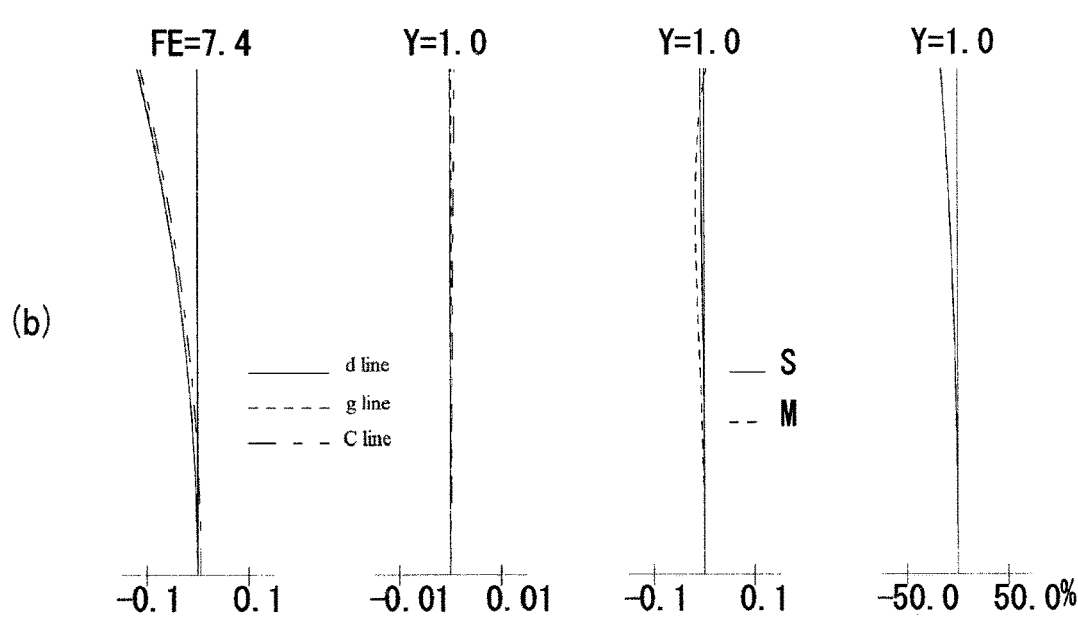

Graphs A to D in FIG. 9(a) are diagrams showing various aberrations when the magnification position is at the wide angle end in the endoscope magnification optical system 100 according to the present Example 4. Graphs A to D in FIG. 9(b) are diagrams showing various aberrations when the magnification position is at the telephoto end in the endoscope magnification optical system 100 according to the present Example 4.

Table 4 shows configurations and specifications using specific numeric values of optical components including the endoscope magnification optical system 100 according to the present Example 4. Note that in Table 4, the group interval between the second lens group G2 and the third lens group G3 is denoted by the reference numeral "D13". As can be understood from FIGS. 8 and 9 and Table 4, the endoscope magnification optical system 100 according to the present Example 4 has a favorable optical performance at any magnification position from the wide angle end to the telephoto end, and has a configuration that is suitable for a solid-state image sensor for a short exit pupil distance.

TABLE 4

Example 4

Image Data

| NO | R | D | N(d) | vd |
|---|---|---|---|---|
| 1 | INFINITY | 0.356 | 1.88300 | 40.8 |
| 2 | 1.300 | 0.600 | | |
| 3 | −1.311 | 0.552 | 1.84666 | 23.8 |
| 4 | −1.597 | 0.089 | | |
| 5 | 1.315 | 0.379 | 1.77250 | 49.6 |
| 6 | 1.585 | D6 | | |
| 7 aperture | INFINITY | 0.082 | | |
| 8 | 2.670 | 0.267 | 1.88300 | 40.8 |
| 9 | 1.871 | 0.623 | 1.84666 | 23.8 |
| 10 | 2.907 | 0.096 | | |
| 11 | −12.488 | 0.267 | 1.84666 | 23.8 |
| 12 | 1.288 | 0.531 | 1.77250 | 49.6 |
| 13 | −1.322 | D13 | | |
| 14 | 4.647 | 0.445 | 1.72916 | 54.7 |
| 15 | 14.634 | 0.429 | | |
| 16 | INFINITY | 1.000 | 1.51407 | 73.4 |
| 17 | INFINITY | 0.200 | 1.51000 | 63.0 |
| 18 | INFINITY | — | | |

Various data

| | Wide angle | Telephoto |
|---|---|---|
| F number | 6.1 | 7.4 |
| Focal length | 1.00 | 1.34 |
| Magnification | −0.091 | −0.531 |
| Half angle of view | 67.9 | 41.1 |
| Image height | 1.00 | 1.00 |
| D6 | 1.161 | 0.120 |
| D13 | 1.047 | 2.088 |

Example 5

Figure 10:
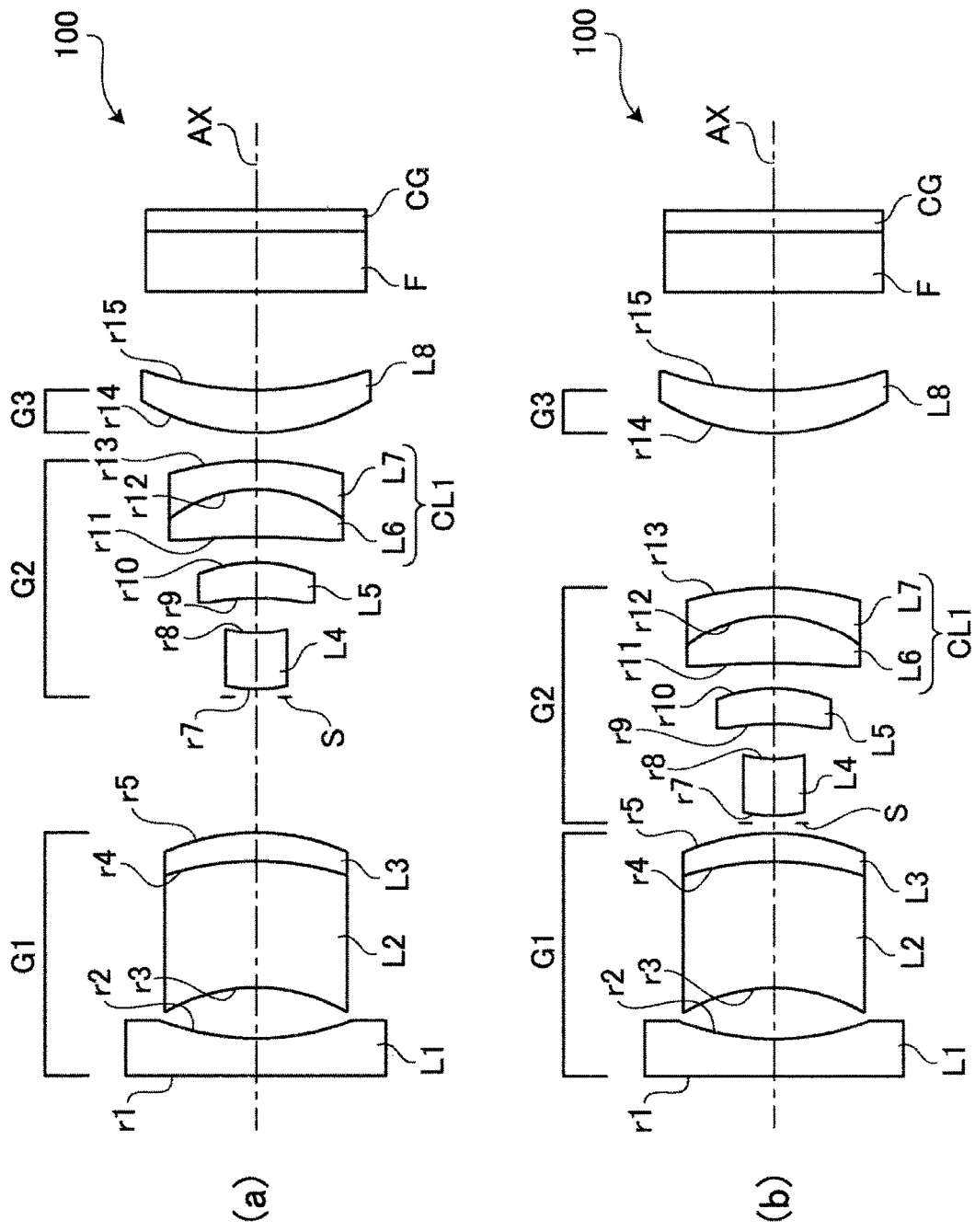
FIG. 10 is a lens arrangement diagram showing a configuration of an endoscope magnification optical system according to Example 5 of the present invention.

FIGS. 10(*a*) and 10(*b*) are cross-sectional views showing an arrangement of optical components including the endoscope magnification optical system 100 according to the present. Example 5. FIG. 10(*a*) shows a lens arrangement when the magnification position is at the wide angle end. FIG. 10(*b*) shows a lens arrangement when the magnification position is at the telephoto end.

Figure 11:
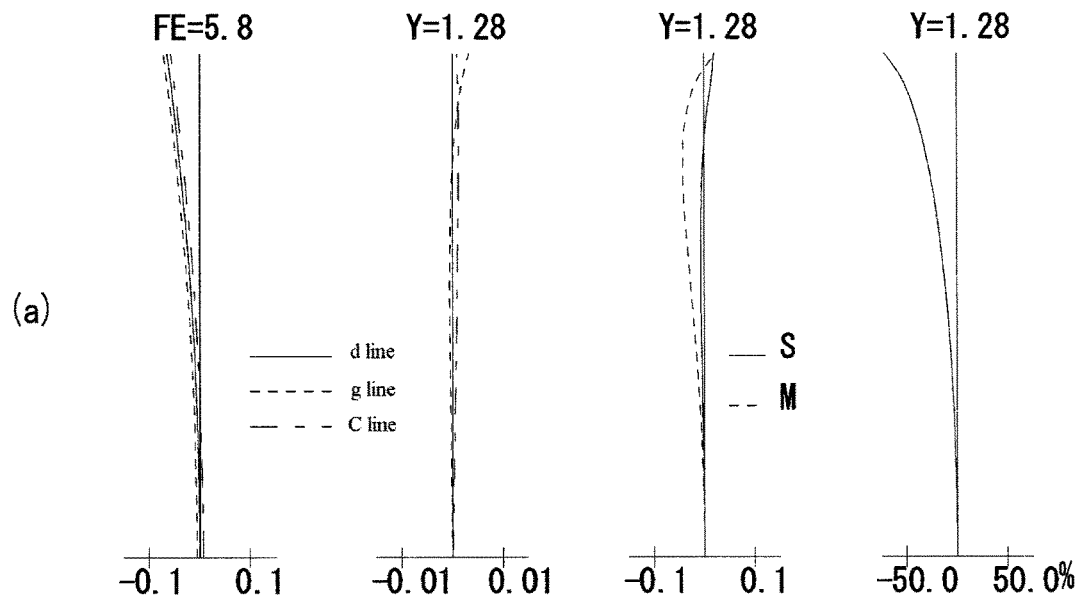
FIG. 11 is a diagram showing various aberrations in the endoscope magnification optical system according to Example 5 of the present invention.
Figure 11:
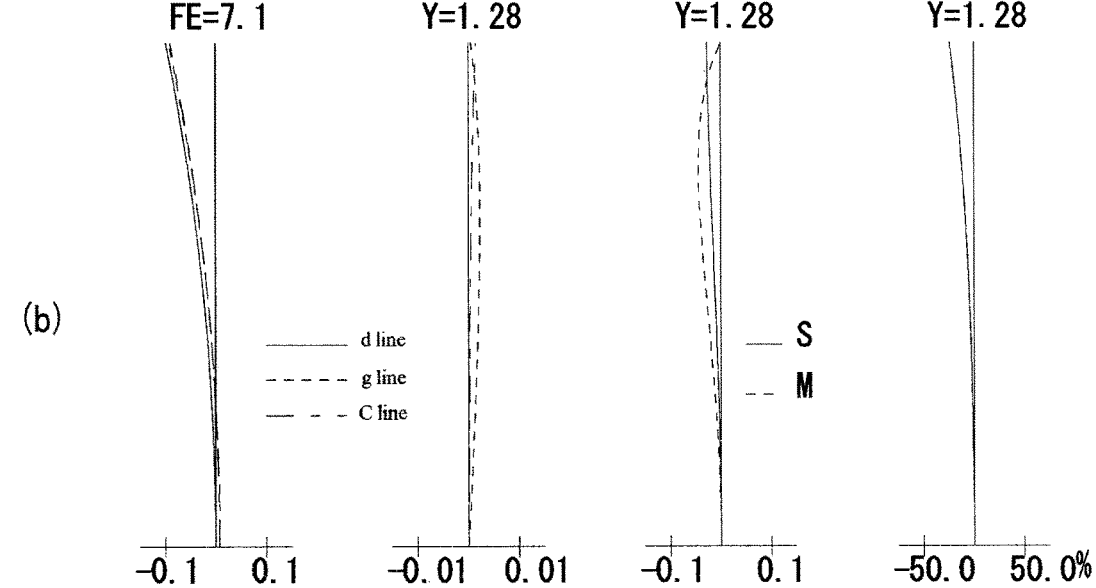

Graphs A to D in FIG. 11(*a*) are diagrams showing various aberrations when the magnification position is at the wide angle end in the endoscope magnification optical system 100 according to the present Example 5. Graphs A to D in FIG. 11(*b*) are diagrams showing various aberrations when the magnification position is at the telephoto end in the endoscope magnification optical system 100 according to the present Example 5.

Table 5 shows configurations and specifications using specific numeric values of optical components including the endoscope magnification optical system 100 according to the present Example 5. Note that in table 5, the group interval between the first lens group G1 and the second lens group G2 is denoted by the reference numeral "D5", and the group interval between the second lens group G2 and the third lens group G3 is denoted by the reference numeral "D13". As can be understood from FIGS. 10 and 11 and Table 5, the endoscope magnification optical system 100 according to the present Example 5 has a favorable optical performance at any magnification position from the wide angle end to the telephoto end, and has a configuration that is suitable for a solid-state image sensor for a short exit pupil distance.

TABLE 5

Example 5

Image Data

| NO | R | D | N(d) | vd |
|---|---|---|---|---|
| 1 | INFINITY | 0.440 | 1.88300 | 40.8 |
| 2 | 3.125 | 0.592 | | |
| 3 | −2.063 | 1.476 | 1.88300 | 40.8 |
| 4 | −3.400 | 0.330 | 1.77250 | 49.6 |
| 5 | −2.596 | D5 | | |
| 6 aperture | INFINITY | 0.088 | | |
| 7 | 1.497 | 0.660 | 1.88300 | 40.8 |
| 8 | 1.420 | 0.411 | | |
| 9 | −3.050 | 0.415 | 1.80400 | 46.6 |
| 10 | −1.740 | 0.296 | | |
| 11 | −9.171 | 0.554 | 1.77250 | 49.6 |
| 12 | −1.659 | 0.330 | 1.95906 | 17.5 |
| 13 | −3.495 | D13 | | |
| 14 | 2.549 | 0.496 | 1.72916 | 54.7 |
| 15 | 3.822 | 1.149 | | |
| 16 | INFINITY | 0.700 | 1.51407 | 73.4 |
| 17 | INFINITY | 0.250 | 1.51000 | 63.0 |
| 18 | INFINITY | — | | |

Various data

| | Wide angle | Telephoto |
|---|---|---|
| F number | 5.8 | 7.1 |
| Focal length | 1.37 | 1.75 |
| Magnification | −0.133 | −0.565 |
| Half angle of view | 74.4 | 43.8 |
| Image height | 1.28 | 1.28 |
| D5 | 1.583 | 0.115 |
| D13 | 0.330 | 1.798 |

Example 6

Figure 12:
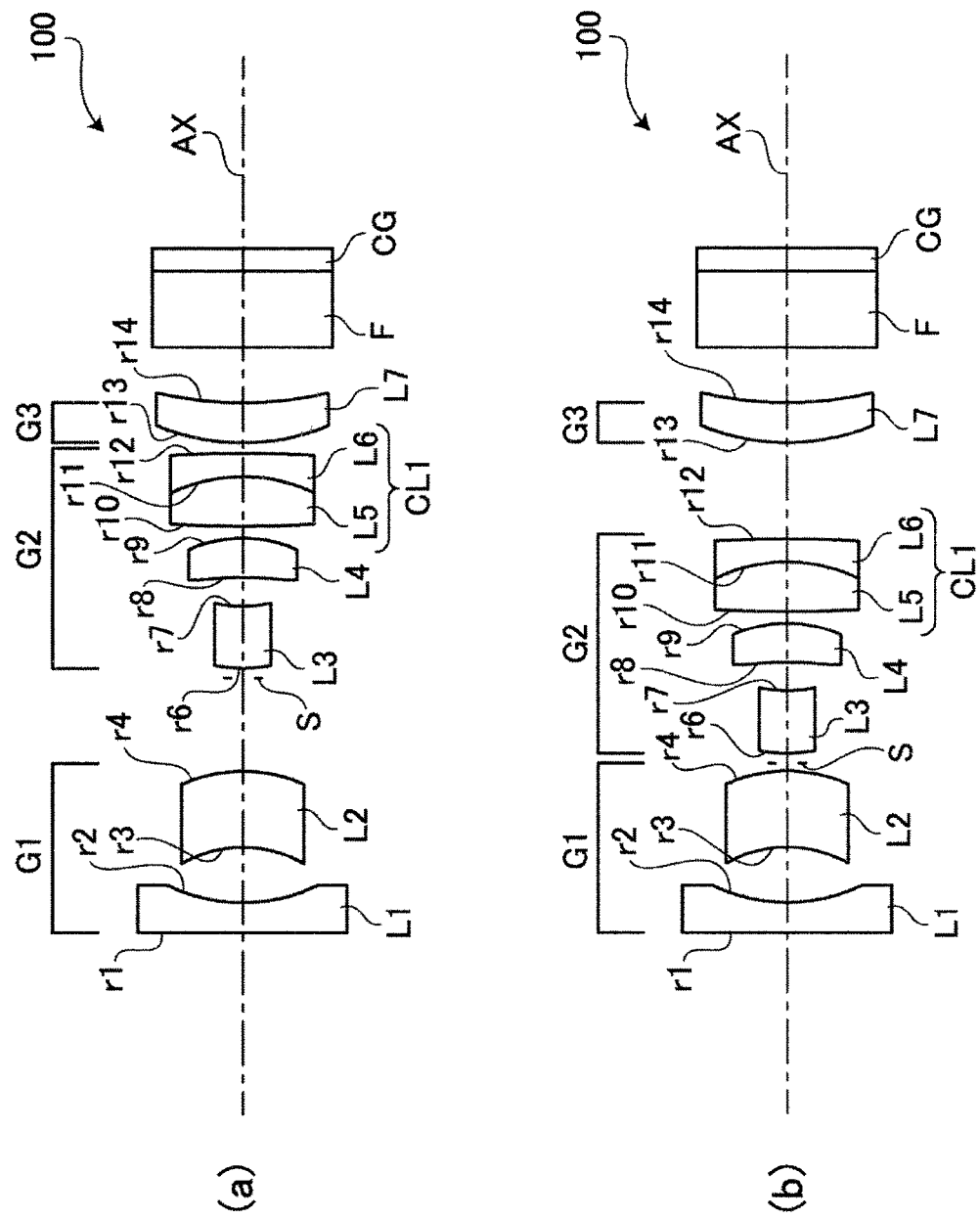
FIG. 12 is a lens arrangement diagram showing a configuration of an endoscope magnification optical system according to Example 6 of the present invention.

FIGS. 12(*a*) and 12(*b*) are cross-sectional views showing an arrangement of optical components including the endoscope magnification optical system 100 according to the present. Example 6. FIG. 12(*a*) shows a lens arrangement when the magnification position is at the wide angle end. FIG. 12(*b*) shows a lens arrangement when the magnification position is at the telephoto end.

Figure 13:
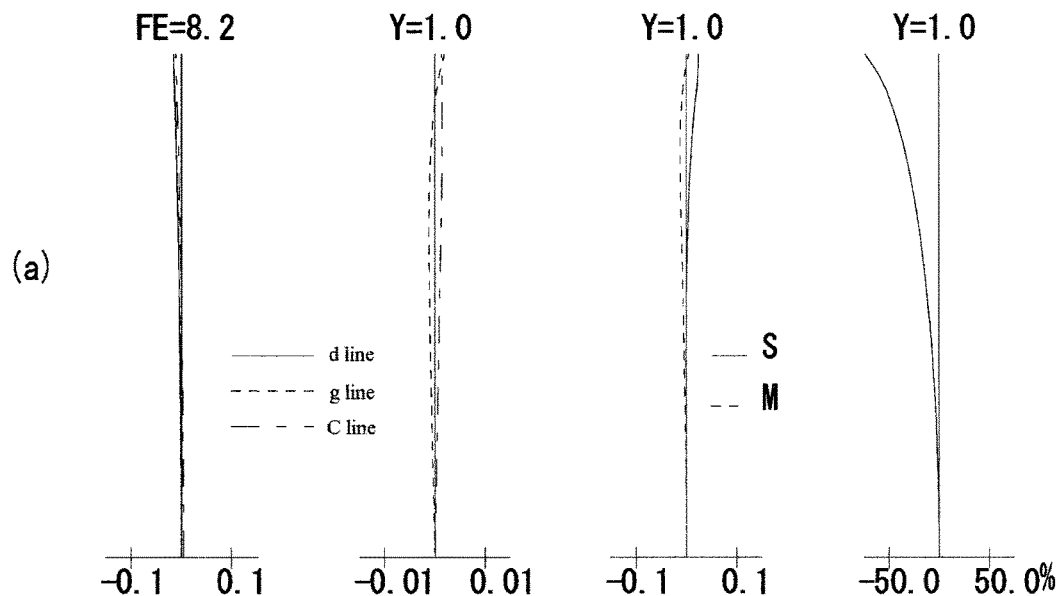
FIG. 13 is a diagram showing various aberrations in the endoscope magnification optical system according to Example 6 of the present invention.
Figure 13:
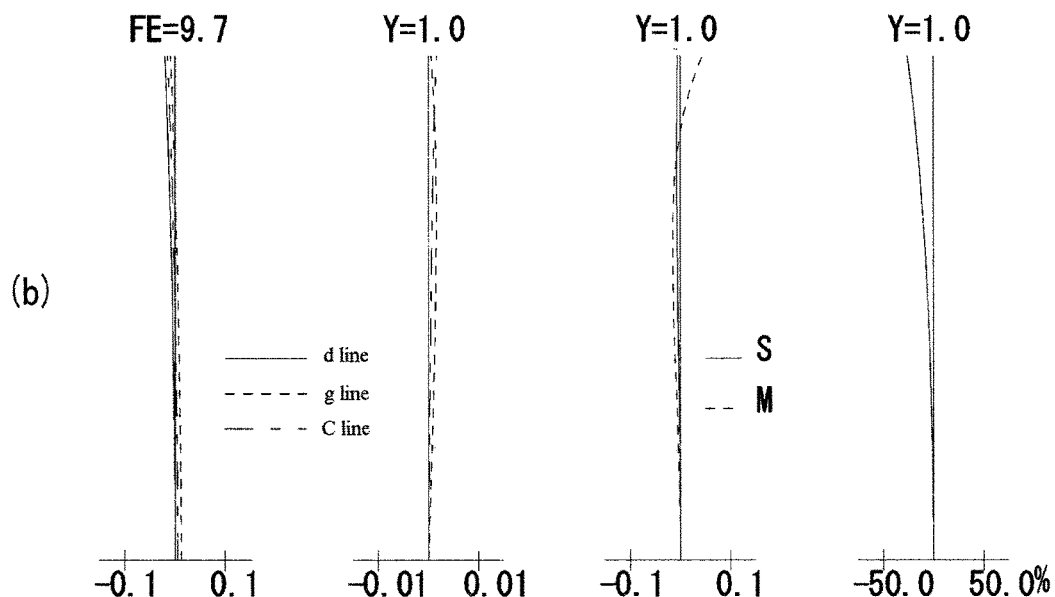

Graphs A to D in FIG. 13(*a*) are diagrams showing various aberrations when the magnification position is at the wide angle end in the endoscope magnification optical system 100 according to the present Example 6. Graphs A to D in FIG. 13(*b*) are diagrams showing various aberrations when the magnification position is at the telephoto end in the endoscope magnification optical system 100 according to the present Example 6.

Table 6 shows configurations and specifications using specific numeric values of optical components including the endoscope magnification optical system 100 according to the present Example 6. Note that in table 6, the group interval between the first lens group G1 and the second lens group G2 is denoted by the reference numeral "D4", and the group interval between the second lens group G2 and the third lens group G3 is denoted by the reference numeral "D12". As can be understood from FIGS. 12 and 13 and Table 6, the endoscope magnification optical system 320 according to the present Example 6 has a favorable optical performance at any magnification position from the wide angle end to the telephoto end, and has a configuration that is suitable for a solid-state image sensor for a short exit pupil distance.

TABLE 6

Example 6

Image Data

| NO | R | D | N(d) | vd |
|---|---|---|---|---|
| 1 | INFINITY | 0.340 | 1.88300 | 40.8 |
| 2 | 1.876 | 0.614 | | |
| 3 | −1.361 | 0.847 | 1.88300 | 40.8 |
| 4 | −1.636 | D4 | | |
| 5 aperture | INFINITY | 0.111 | | |
| 6 | 1.592 | 0.695 | 1.88300 | 40.8 |
| 7 | 1.465 | 0.315 | | |
| 8 | −4.358 | 0.434 | 1.80400 | 46.6 |
| 9 | −1.471 | 0.131 | | |
| 10 | 12.713 | 0.548 | 1.88300 | 40.8 |
| 11 | −1.853 | 0.255 | 1.95906 | 17.5 |
| 12 | −14.011 | D12 | | |
| 13 | 2.509 | 0.441 | 1.72916 | 54.7 |
| 14 | 4.185 | 0.618 | | |
| 15 | INFINITY | 0.850 | 1.51407 | 73.4 |
| 16 | INFINITY | 0.255 | 1.51000 | 64.1 |
| 17 | INFINITY | — | | |

Various data

| | Wide angle | Telephoto |
|---|---|---|
| F number | 8.2 | 9.7 |
| Focal length | 1.00 | 1.28 |
| Magnification | −0.106 | −0.460 |
| Half angle of view | 75.9 | 46.4 |
| Image height | 1.00 | 1.00 |
| D4 | 1.030 | 0.085 |
| D12 | 0.116 | 1.062 |

Example 7

Figure 14:
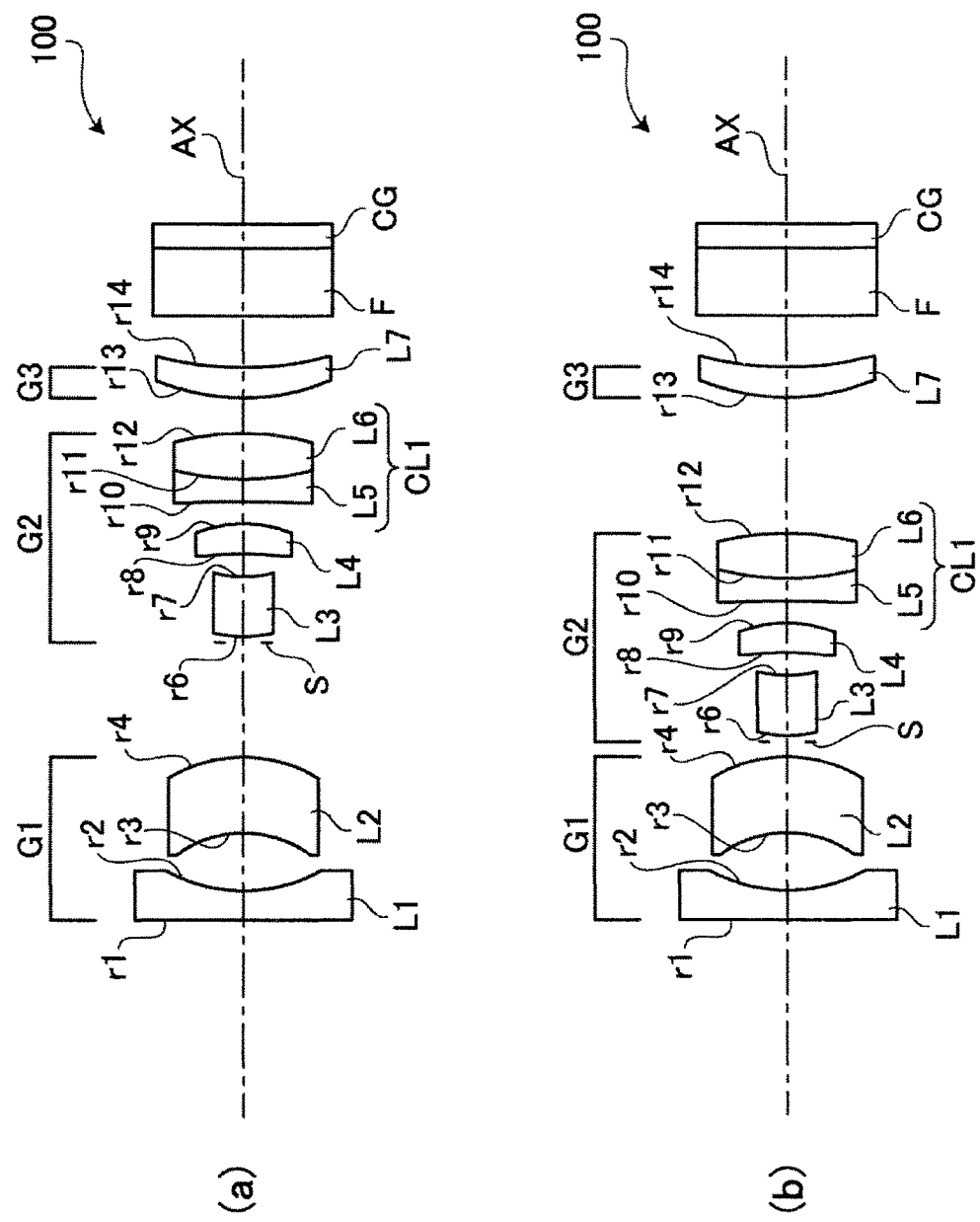
FIG. 14 is a lens arrangement diagram showing a configuration of an endoscope magnification optical system according to Example 7 of the present invention.

FIGS. 14(a) and 14(b) are cross-sectional views showing an arrangement of optical components including the endoscope magnification optical system 100 according to the present Example 7. FIG. 14(a) shows a lens arrangement when the magnification position is at the wide angle end. FIG. 14(b) shows a lens arrangement when the magnification position is at the telephoto end.

Figure 15:
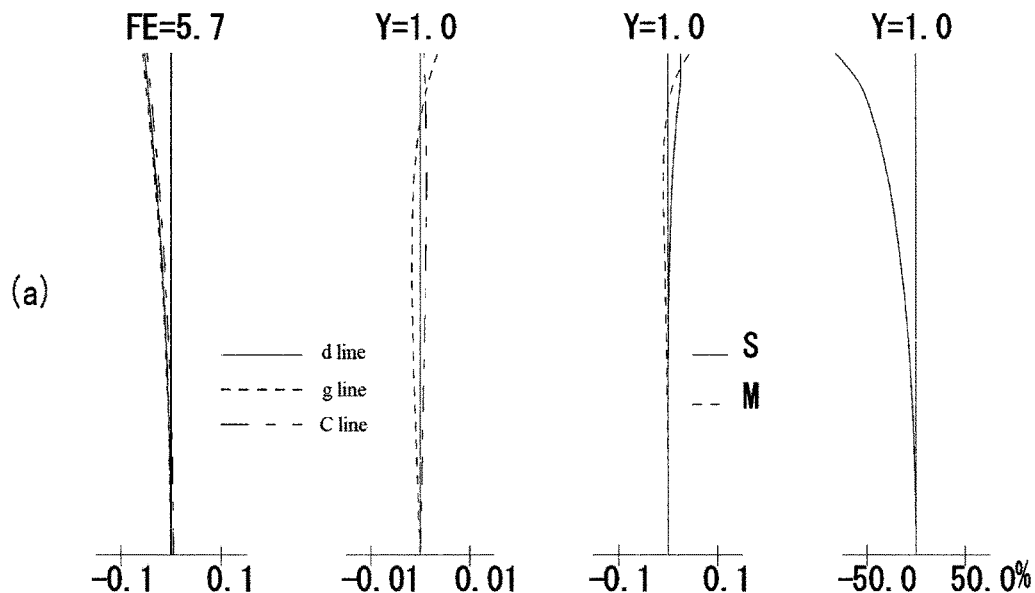
FIG. 15 is a diagram showing various aberrations in the endoscope magnification optical system according to Example 7 of the present invention.
Figure 15:
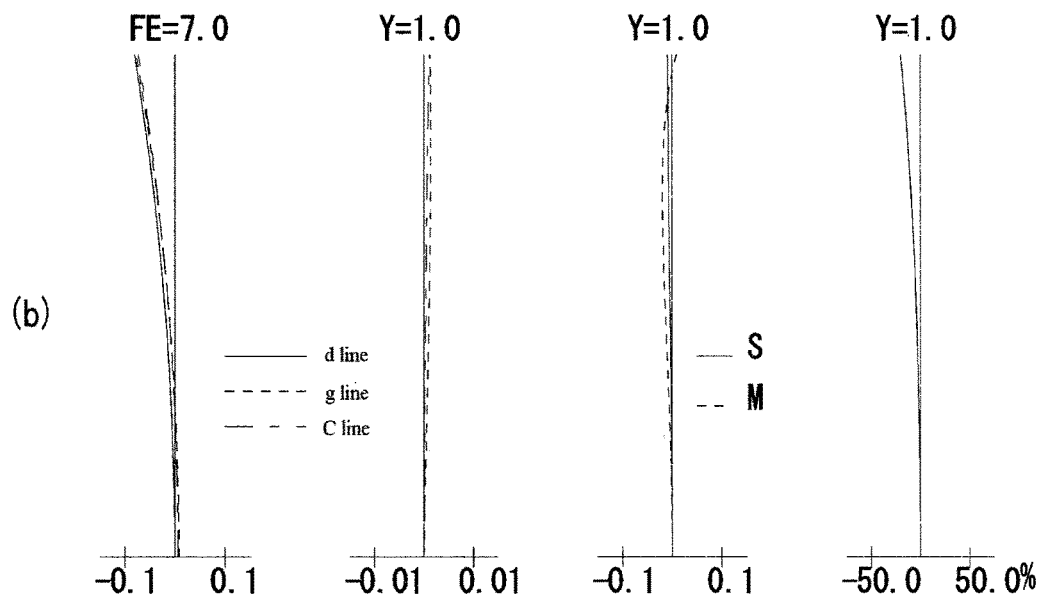

Graphs A to D in FIG. 15(a) are diagrams showing various aberrations when the magnification position is at the wide angle end in the endoscope magnification optical system 100 according to the present Example 7. Graphs A to D in FIG. 15(b) are diagrams showing various aberrations when the magnification position is at the telephoto end in the endoscope magnification optical system 100 according to the present Example 7.

Table 7 shows configurations and specifications using specific numeric values of optical components including the endoscope magnification optical system 100 according to the present Example 7. Note that in table 7, the group interval between the first lens group G1 and the second lens group G2 is denoted by the reference numeral "D4", and the group interval between the second lens group G2 and the third lens group G3 is denoted by the reference numeral "D12". As can be understood from FIGS. 14 and 15 and Table 7, the endoscope magnification optical system 540 according to the present Example 7 has a favorable optical performance at any magnification position from the wide angle end to the telephoto end, and has a configuration that is suitable for a solid-state image sensor for a short exit pupil distance.

TABLE 7

Example 7

Image Data

| NO | R | D | N(d) | vd |
|---|---|---|---|---|
| 1 | INFINITY | 0.336 | 1.88300 | 40.8 |
| 2 | 1.819 | 0.637 | | |
| 3 | −1.257 | 0.838 | 1.88300 | 40.8 |
| 4 | −1.589 | D4 | | |
| 5 aperture | INFINITY | 0.067 | | |
| 6 | 1.427 | 0.670 | 1.88300 | 40.8 |
| 7 | 1.387 | 0.251 | | |
| 8 | −3.590 | 0.335 | 1.80400 | 46.6 |
| 9 | −1.410 | 0.243 | | |
| 10 | −12.863 | 0.251 | 1.95906 | 17.5 |
| 11 | 3.069 | 0.503 | 1.77250 | 49.6 |
| 12 | −3.069 | D12 | | |
| 13 | 2.546 | 0.335 | 1.72916 | 54.7 |
| 14 | 3.875 | 0.674 | | |
| 15 | INFINITY | 0.750 | 1.51407 | 73.4 |
| 16 | INFINITY | 0.255 | 1.51000 | 63.0 |
| 17 | INFINITY | — | | |

Various data

| | Wide angle | Telephoto |
|---|---|---|
| F number | 5.7 | 7.0 |
| Focal length | 0.99 | 1.32 |
| Magnification | −0.106 | −0.562 |
| Half angle of view | 80.5 | 42.9 |
| Image height | 1.00 | 1.00 |
| D4 | 1.274 | 0.167 |
| D12 | 0.396 | 1.502 |

Conditional Equation Verification

Table 8 is a list of values calculated when the conditional equations (1) to (7) are applied to the Examples 1 to 7.

TABLE 8

(Conditional equation evaluation)

| Conditional equation | Ex. 1 | Ex. 2 | Ex. 3 | Ex. 4 | Ex. 5 | Ex. 6 | Ex. 7 |
|---|---|---|---|---|---|---|---|
| (1) $m_{2w}$ | −0.455 | −0.469 | −0.366 | −0.408 | −0.389 | −0.468 | −0.469 |
| (1) $m_{2t}$ | −0.954 | −0.983 | −0.853 | −0.945 | −0.823 | −0.873 | −0.949 |
| (2)(3) $f_3/f_w$ | 7.6 | 8.3 | 4.4 | 9.2 | 6.6 | 7.7 | 9.3 |
| (4)(5) $f_2/f_3$ | 0.29 | 0.27 | 0.61 | 0.24 | 0.38 | 0.30 | 0.25 |
| (6)(7) $\lvert f_3/f_1 \rvert$ | 2.43 | 2.78 | 0.81 | 3.11 | 1.39 | 2.27 | 3.04 |

The endoscope magnification optical system 100 according to the Examples 1, 2, and 4 to 7 satisfy the conditional equations (1) to (7) as shown in Table 8. Also, the endoscope magnification optical system 100 according to the Example 3 satisfies the conditional equations (1), (2), (4), and (6) as shown in Table 8. Accordingly, in the Examples 1 to 7, further effects are achieved due to the conditional equations being satisfied.

The foregoing is a description of an illustrative embodiment of the present invention. The embodiment of the present invention is not limited to the content described above, and various modifications are possible within the scope of the technical idea of the present invention. For example, the embodiment of the present application also encompasses content obtained by combining, as appropriate, the embodiment disclosed illustratively in the specification, an obvious embodiment, and the like.

The invention claimed is:

1. An endoscope magnification optical system, comprising, in order from an object side:
    a first lens group having a negative power; a second lens group having a positive power; and a third lens group consisting of a meniscus lens having a positive power and a convex surface facing the object side,
    wherein a distance from a lens surface of the first lens group that is nearest to the object side to an image surface is kept constant while the second lens group is moved in an optical axis direction with respect to the first lens group and the third lens group, which are fixed lens groups, and thereby an optical image is magnified, and
    wherein if the focal length of the third lens group is defined as $f_3$ (units: mm) and the composite focal length of first to third lens groups at the wide angle end is defined as $f_w$ (units: mm), the following equation is satisfied:

$4 \leq f_3/f_w \leq 11$.

2. The endoscope magnification optical system according to claim 1, wherein
    if the magnification of the second lens group at a telephoto end is defined as $m_{2t}$ and the magnification of the second lens group at a wide angle end is defined as $m_{2w}$, the following conditional equation is satisfied:

$-1 < m_{2t} < m_{2w} < -0.35$.

3. The endoscope magnification optical system according to claim 1, wherein
    the following conditional equation is satisfied:

$6 < f_3/f_w < 10$.

4. The endoscope magnification optical system according to claim 1, wherein
    the first lens group includes two lenses having negative powers, and a lens having a positive power.

5. The endoscope magnification optical system according to claim 1, wherein
    if the focal length of the second lens group is defined as $f_2$ (units: mm) and the focal length of the third lens group is defined as $f_3$ (units: mm), the following equation is satisfied:

$0.2 < f_2/f_3 < 0.7$.

6. The endoscope magnification optical system according to claim 5, wherein
    the following conditional equation is satisfied:

$0.2 < f_2/f_3 < 0.4$.

7. The endoscope magnification optical system according to claim 1, wherein
    if the focal length of the first lens group is defined as $f_1$ (units: mm) and the focal length of the third lens group is defined as $f_3$ (units: mm), the following equation is satisfied:

$0.7 < |f_3/f_1| < 3.5$.

8. The endoscope magnification optical system according to claim 7, wherein
    the following conditional equation is satisfied:

$1.2 < |f_3/f_1| < 3.2$.

9. The endoscope magnification optical system according to claim 1, comprising
    an aperture configured to move integrally with the second lens group on an optical axis between the first and the second lens groups.

10. An endoscope, wherein
    an endoscope magnification optical system according to claim 1 is incorporated at a leading end of the endoscope.

11. An endoscope system comprising:
    the endoscope according to claim 10;
    a light source apparatus configured to supply irradiated light to the endoscope; and
    an image processing apparatus configured to process an image signal output by the endoscope.

* * * * *